United States Patent
Armstrong et al.

(10) Patent No.: US 10,829,686 B2
(45) Date of Patent: Nov. 10, 2020

(54) QUANTUM DOTS WITH STABILIZING FLUOROCHEMICAL AGENTS

(71) Applicant: 3M INNOVATIVE PROPERTIES COMPANY, St. Paul, MN (US)

(72) Inventors: Paul B. Armstrong, St. Paul, MN (US); Saswata Chakraborty, Cottage Grove, MN (US); Michael C. Palazzotto, Woodbury, MN (US); Guy D. Joly, Shoreview, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 131 days.

(21) Appl. No.: 16/090,514

(22) PCT Filed: Mar. 23, 2017

(86) PCT No.: PCT/US2017/023700
§ 371 (c)(1),
(2) Date: Oct. 1, 2018

(87) PCT Pub. No.: WO2017/172462
PCT Pub. Date: Oct. 5, 2017

(65) Prior Publication Data
US 2019/0359883 A1 Nov. 28, 2019

Related U.S. Application Data

(60) Provisional application No. 62/316,863, filed on Apr. 1, 2016.

(51) Int. Cl.
*C09K 11/02* (2006.01)
*C07C 43/12* (2006.01)
*C07F 9/50* (2006.01)
*C09K 11/70* (2006.01)
*B82Y 20/00* (2011.01)

(52) U.S. Cl.
CPC ............ *C09K 11/025* (2013.01); *C07C 43/12* (2013.01); *C07F 9/5022* (2013.01); *C09K 11/703* (2013.01); *B82Y 20/00* (2013.01)

(58) Field of Classification Search
CPC ....... C09K 11/25; C09K 11/703; B82Y 20/00; C07C 43/12; C07F 9/5022
See application file for complete search history.

(56) References Cited

U.S. PATENT DOCUMENTS

| | | |
|---|---|---|
| 3,250,808 A | 5/1966 | Moore |
| 3,705,208 A | 12/1972 | Nakamuta |
| 3,708,296 A | 1/1973 | Schlesinger |
| 4,069,055 A | 1/1978 | Crivello |
| 4,216,288 A | 8/1980 | Crivello |
| 4,250,311 A | 2/1981 | Crivello |
| 4,857,434 A | 8/1989 | Klinger |
| 5,084,586 A | 1/1992 | Farooq |
| 5,124,417 A | 6/1992 | Farooq |
| 5,462,835 A | 10/1995 | Mirle |
| 5,587,433 A | 12/1996 | Boeckeler |
| 6,451,958 B1 | 9/2002 | Fan |
| 6,777,460 B2 | 8/2004 | Palazzotto |
| 6,949,206 B2 | 9/2005 | Whiteford |
| 7,018,713 B2 | 3/2006 | Padiyath |
| 7,160,613 B2 | 1/2007 | Bawendi |
| 8,283,412 B2 | 10/2012 | Liu |
| 8,848,132 B2 | 9/2014 | O'Neill |
| 2002/0022709 A1 | 2/2002 | Mader |

(Continued)

FOREIGN PATENT DOCUMENTS

| | | | |
|---|---|---|---|
| JP | 2015-127733 | | 7/2015 |
| WO | WO 2009/051337 | * | 4/2009 |

(Continued)

OTHER PUBLICATIONS

Friesen et al ,"The first fluorous biphase hydrogenation catalyst incorporating a perfluoropolyakylether: [RhCl(PPh2(C6H4C(O)OCH2CF(CF3)(OCF2CF(CF3))nF))3] with n=4-9", Journal of Fluorine Chemistry, vol. 144 (2012), Sep. 10, 2012, pp. 24-32.*
Alivisatos, "Semiconductor Clusters, Nanocrystals, and Quantum Dots", Science, New Series, vol. 271, No. 5251, Feb. 16, 1996, pp. 933-937, American Association for the Advancement of Science.
Peng et al., "Epitaxial Growth of Highly Luminescent CdSe/CdS Core/Shell Nanocrystals with Photostability and Electronic Accessibility", J. Am. Chem. Soc., 1997, 119, pp. 7019-7029.
Murray et al., "Synthesis and Characterization of Nearly Monodisperse CdE (E=S, Se, Te) Semiconductor Nanocrystallites", J. Am. Chem. Soc., 1993, 115 (19), pp. 8706-8715.

(Continued)

*Primary Examiner* — C Melissa Koslow
(74) *Attorney, Agent, or Firm* — Lisa P. Fulton

(57) ABSTRACT

Disclosed are quantum dots and quantum dot articles stabilized by a stabilizing agent of the formula:

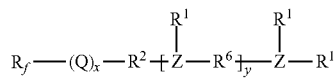

wherein each $R^1$ is a hydrocarbyl group including alkyl, aryl, alkaryl and aralkyl;
$R^2$ is a divalent hydrocarbyl group selected from alkylene, arylene, alkarylene and aralkylene;
Z is P, As or Sb;
Q is —$CH_2$—S—, —$CH_2$—O—, —$CO_2$—, —$CH2$—O—CO—, —$CONR^3$—, —NH—CO—$NR^3$—, and —$NR^3$,
where $R^3$ is H or $C_1$-$C_4$ alkyl,
subscript x is 1,
$R^6$ is a divalent hydrocarbyl group selected from alkylene, arylene, alkarylene and aralkylene,
subscript y is 0 or 1,
$R_f$ is a perfluoroether group.

24 Claims, 3 Drawing Sheets

(56) References Cited

U.S. PATENT DOCUMENTS

2014/0287248 A1 9/2014 Flynn
2018/0044582 A1 2/2018 Qiu
2018/0057658 A1 3/2018 Qiu

FOREIGN PATENT DOCUMENTS

| WO | WO 2010/003059 | 1/2010 |
| WO | WO 2010/039897 | 4/2010 |
| WO | WO 2015/095032 | 6/2015 |
| WO | WO 2015/095296 | 6/2015 |
| WO | WO 2015/138174 | 9/2015 |
| WO | WO 2016/081219 | 5/2016 |
| WO | WO 2017/106613 | 6/2017 |

OTHER PUBLICATIONS

Dabbousi et al., "(CdSe)ZnS Core-Shell Quantun Dots: Synthesis and Characterization of a Size Series of Highly Luminescent Nanocrystallites", J. Phys. Chem. B, 1997, 101, pp. 9463-9475.

Hines et al., "Synthesis and Characterization of Strongly Luminescing ZnS-Capped CdSe Nanocrystals", J. Phys. Chem., 1996, 100, pp. 468-471.

J V. Crivello & K. Dietliker, "Photoinitiators for Free Radical Cationic & Anionic Photopolymerization", 2nd Edition, John Wiley and Sons, 1998, pp. 275 to 298.

\* cited by examiner

QUANTUM DOTS WITH STABILIZING FLUOROCHEMICAL AGENTS

BACKGROUND

Quantum Dot Enhancement Films (QDEF) are used as part of the backlight for LCD displays. Red and green quantum dots in the film down-convert light from the blue LED source to give white light. This has the advantage of improving the color gamut over the typical LCD display and keeping the energy consumption low compared to LED displays.

Colloidal quantum dot nanoparticles (preferably, nanocrystals) are stabilized with organic ligands and/or additives to maintain dispersion stability in a carrier fluid (or solvent). Quantum dot ligands also improve photoluminescent quantum yields by passivating surface traps, stabilize against aggregation and degradation, and influence the kinetics of nanoparticle (preferably, nanocrystal) growth during synthesis. Therefore, optimizing the organic ligand and/or additive is important for achieving optimal quantum yield, processability, and functional lifetime in QDEF.

SUMMARY

Composite particles are provided that are capable of fluorescence and suitable for use in quantum dot enhancement films.

In one aspect, the present disclosure provides a composite particle that includes: a fluorescent semiconductor core/shell nanoparticle (preferably, nanocrystal); and a stabilizing agent combined with the core/shell nanoparticle, the stabilizing agent comprising a molecule having perfluoroether groups and phosphine, arsine or stibine groups.

The stabilizing agent is of the formula:

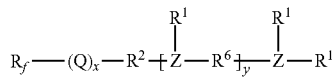

wherein each $R^1$ is a hydrocarbyl group including alkyl, aryl, alkaryl and aralkyl;
$R^2$ is a divalent hydrocarbyl group selected from alkylene, arylene, alkarylene and aralkylene;
Z is P, As or Sb;
Q is —$CH_2$—S—, —$CH_2$—O—, —$CO_2$—, —$CONR^3$—, —$CH_2$—O—CO—, —NH—CO—$NR^3$—, and —$NR^3$,
where $R^3$ is H or $C_1$-$C_4$ alkyl, and subscript x is 1,
$R^6$ is a divalent hydrocarbyl group selected from alkylene, arylene, alkarylene and aralkylene,
subscript y is 0 or 1, and
$R_f$ is a perfluoropolyether group.

In one aspect, the present disclosure provides a composite particle that includes: a fluorescent semiconductor core/shell nanoparticle (preferably, nanocrystal); and a stabilizing agent having 1) pendent phosphine, arsine or stibine groups, and 2) perfluoropolyether groups, that is combined with, attached to, or associated with, the core/shell nanoparticle.

In a preferred embodiment, the fluorescent semiconductor core/shell nanoparticle includes: an InP core; an inner shell overcoating the core, wherein the inner shell includes zinc selenide and zinc sulfide; and an outer shell overcoating the inner shell, wherein the outer shell includes zinc sulfide.

In another aspect, the present disclosure provides a composition comprising
a. 1 to 10 parts by weight of fluorescent nanoparticles,
b. 1 to 40 parts by weight of a stabilizing agent of the formula:

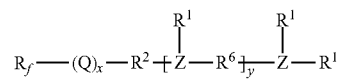

wherein each $R^1$ is a hydrocarbyl group including alkyl, aryl, alkaryl and aralkyl;
$R^2$ is a divalent hydrocarbyl group selected from alkylene, arylene, alkarylene and aralkylene;
Z is P, As or Sb;
Q is —$CH_2$—S—, —$CH_2$—O—, —$CO_2$—, —$CH_2$—O—CO—, —$CONR^3$—, —NH—CO—$NR^3$—, and —$NR^3$,
where $R^3$ is H or $C_1$-$C_4$ alkyl, and subscript x is 1, and
$R^6$ is a divalent hydrocarbyl group selected from alkylene, arylene, alkarylene and aralkylene,
subscript y is 0 or 1,
$R_f$ is a perfluoroether group, and
c. 5 to 50 parts by weight of a secondary perfluorinated carrier fluid.

In some preferred embodiments, the above composition is dispersed in a polymeric binder.

As used herein

"Alkyl" means a linear or branched, cyclic or acylic, saturated monovalent hydrocarbon.

"Alkylene" means a linear or branched unsaturated divalent hydrocarbon.

"Alkenyl" means a linear or branched unsaturated hydrocarbon.

"Aryl" means a monovalent aromatic, such as phenyl, naphthyl and the like.

"Arylene" means a polyvalent, aromatic, such as phenylene, naphthalene, and the like.

"Aralkylene" means a group defined above with an aryl group attached to the alkylene, e.g., benzyl, 1-naphthylethyl, and the like.

As used herein, "(hetero)hydrocarbyl" is inclusive of hydrocarbyl alkyl, aryl, aralkyl and alkaryl groups, and heterohydrocarbyl heteroalkyl and heteroaryl groups, the later comprising one or more catenary (in-chain) heteroatoms such as ether or amino groups. Heterohydrocarbyl may optionally contain one or more catenary (in-chain) functional groups including ester, amide, urea, urethane, and carbonate functional groups.

Unless otherwise indicated, the non-polymeric (hetero)hydrocarbyl groups typically contain from 1 to 60 carbon atoms. Some examples of such heterohydrocarbyls as used herein include, but are not limited to, methoxy, ethoxy, propoxy, 4-diphenylaminobutyl, 2-(2'-phenoxyethoxy)ethyl, 3,6-dioxaheptyl, 3,6-dioxahexyl-6-phenyl, in addition to those described for "alkyl", "heteroalkyl", and "aryl" supra.

The term "composite particle" as used herein refers to a nanoparticle, which is typically in the form of a core/shell nanoparticle (preferably, nanocrystal), having any associated organic coating or other material on the surface of the nanoparticle that is not removed from the surface by ordinary solvation. Such composite particles are useful as "quantum dots," which have a tunable emission in the near ultraviolet (UV) to far infrared (IR) range as a result of the use of a semiconductor material.

The term "nanoparticle" refers to a particle having an average particle diameter in the range of 0.1 to 1000 nanometers such as in the range of 0.1 to 100 nanometers or in the range of 1 to 100 nanometers. The term "diameter" refers not only to the diameter of substantially spherical particles but also to the distance along the smallest axis of the structure. Suitable techniques for measuring the average particle diameter include, for example, scanning tunneling microscopy, light scattering, and transmission electron microscopy.

A "core" of a nanoparticle is understood to mean a nanoparticle (preferably, a nanocrystal) to which no shell has been applied or to the inner portion of a core/shell nanoparticle. A core of a nanoparticle can have a homogenous composition or its composition can vary with depth inside the core. Many materials are known and used in core nanoparticles, and many methods are known in the art for applying one or more shells to a core nanoparticle. The core has a different composition than the one more shells. The core typically has a different chemical composition than the shell of the core/shell nanoparticle.

DETAILED DESCRIPTION

Figure 1:
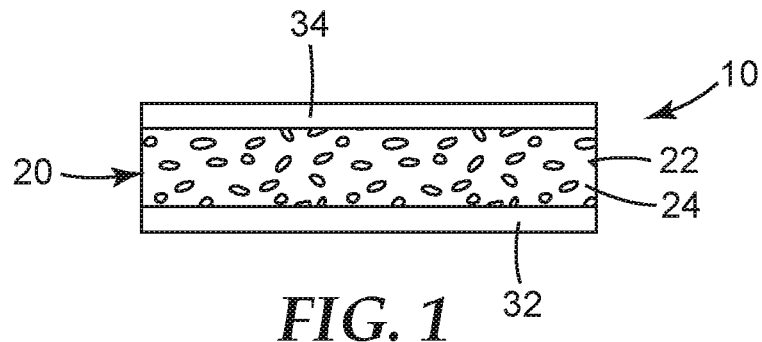
FIG. 1 is a schematic side elevation view of an edge region of an illustrative film article including quantum dots.

The present disclosure provides composite particles that contain fluorescent semiconductor nanoparticles that can fluoresce when excited with actinic radiation. The composite particles can be used in coatings and films for use in optical displays.

Fluorescent semiconductor nanoparticles emit a fluorescence signal when suitably excited. They fluoresce at a second wavelength of actinic radiation when excited by a first wavelength of actinic radiation that is shorter than the second wavelength. In some embodiments, the fluorescent semiconductor nanoparticles can fluoresce in the visible region of the electromagnetic spectrum when exposed to wavelengths of light in the ultraviolet region of the electromagnetic spectrum. In other embodiments, the fluorescent semiconductor nanoparticles can fluoresce in the infrared region when excited in the ultraviolet or visible regions of the electromagnetic spectrum. In still other embodiments, the fluorescent semiconductor nanoparticles can fluoresce in the ultraviolet region when excited in the ultraviolet region by a shorter wavelength of light, can fluoresce in the visible region when excited by a shorter wavelength of light in the visible region, or can fluoresce in the infrared region when excited by a shorter wavelength of light in the infrared region. The fluorescent semiconductor nanoparticles are often capable of fluorescing in a wavelength range such as, for example, at a wavelength up to 1200 nanometers (nm), or up to 1000 nm, up to 900 nm, or up to 800 nm. For example, the fluorescent semiconductor nanoparticles are often capable of fluorescence in the range of 400 to 800 nanometers.

The nanoparticles have an average particle diameter of at least 0.1 nanometer (nm), or at least 0.5 nm, or at least 1 nm. The nanoparticles have an average particle diameter of up to 1000 nm, or up to 500 nm, or up to 200 nm, or up to 100 nm, or up to 50 nm, or up to 20 nm, or up to 10 nm. Semiconductor nanoparticles, particularly with sizes on the scale of 1-10 nm, have emerged as a category of the most promising advanced materials for cutting-edge technologies.

Semiconductor materials include elements or complexes of Group 2-Group 16, Group 12-Group 16, Group 13-Group 15, Group 14-Group 16, and Group 14 semiconductors of the Periodic Table (using the modern group numbering system of 1-18). Some suitable quantum dots include a metal phosphide, a metal selenide, a metal telluride, or a metal sulfide. Exemplary semiconductor materials include, but are not limited to, Si, Ge, Sn, BN, BP, BAs, AlN, AlP, AlAs, AlSb, GaN, GaP, GaAs, GaSb, InN, InP, InAs, InSb, AlN, AlP, AlAs, AlSb, GaN, GaP, GaAs, GaSb, ZnO, ZnS, ZnSe, ZnTe, CdS, CdSe, CdTe, HgS, HgSe, HgTe, BeS, BeSe, BeTe, MgS, MgSe, MgTe, GeS, GeSe, GeTe, SnS, SnSe, SnTe, PbO, PbS, PbSe, PbTe, CuF, CuCl, CuBr, CuI, $Si_3N_4$, $Ge_3N_4$, $Al_2O_3$, $(Ga,In)_2(S,Se,Te)_3$, $Al_2CO$, CaS, CaSe, CaTe, SrS, SrSe, SrTe, BaS, BaSe, BaTe, and an appropriate combination of two or more such semiconductors. These semiconductor materials can be used for the core, the one or more shell layers, or both.

In certain embodiments, exemplary metal phosphide quantum dots include indium phosphide and gallium phosphide, exemplary metal selenide quantum dots include cadmium selenide, lead selenide, and zinc selenide, exemplary metal sulfide quantum dots include cadmium sulfide, lead sulfide, and zinc sulfide, and exemplary metal telluride quantum dots include cadmium telluride, lead telluride, and zinc telluride. Other suitable quantum dots include gallium arsenide and indium gallium phosphide. Exemplary semiconductor materials are commercially available from Evident Thermoelectrics (Troy, N.Y.), and from Nanosys Inc., Milpitas, Calif.

Nanocrystals (or other nanostructures) for use in the present invention can be produced using any method known to those skilled in the art. Suitable methods are disclosed in U.S. Pat. No. 6,949,206 (Whiteford, incorporated by reference herein in their entireties. The nanocrystals (or other nanostructures) for use in the present invention can be produced from any suitable material, suitably an inorganic material, and more suitably an inorganic conductive or semiconductive material. Suitable semiconductor materials include those disclosed in and include any type of semiconductor, including group 12-16, group 13-15, group 14-16 and group 14 semiconductors.

Suitable semiconductor materials include, but are not limited to, Si, Ge, Sn, Se, Te, B, C (including diamond), P, BN, BP, BAs, AlN, AlP, AlAs, AlSb, GaN, GaP, GaAs, GaSb, InN, InP, InAs, InSb, AlN, AlP, As, AlSb, GaN, GaP, GaAs, GaSb, ZnO, ZnS, ZnSe, ZnTe, CdS, CdSe, CdTe, HgS, HgSe, HgTe, BeS, BeSe, BeTe, MgS, MgSe, GeS, GeSe, GeTe, SnS, SnSe, SnTe, PbO, PbS, PbSe, PbTe, CuF, CuCl, CuBr, CuI, $Si_3N_4$, $Ge_3N_4$, $Al_2O_3$, $(Ga, In)_2(S, Se, Te)_3$, $Al_2CO$, and an appropriate combination of two or more such semiconductors.

In certain aspects, the semiconductor nanocrystals or other nanostructures may comprise a dopant from the group consisting of: a p-type dopant or an n-type dopant. The nanocrystals (or other nanostructures) useful in the present invention can also comprise Group 12-Group 16 or Group 13-Group 15 semiconductors. Examples of Group 12-Group 16 or Group 13-Group 15 semiconductor nanocrystals and nanostructures include any combination of an element from Group 12, such as Zn, Cd and Hg, with any element from Group 16, such as S, Se, Te, Po, of the Periodic Table; and any combination of an element from Group 13, such as B, Al, Ga, In, and Tl, with any element from Group 15, such as N, P, As, Sb and Bi, of the Periodic Table.

Other suitable inorganic nanostructures include metal nanostructures. Suitable metals include, but are not limited to, Ru, Pd, Pt, Ni, W, Ta, Co, Mo, Ir, Re, Rh, Hf, Nb, Au, Ag, Ti, Sn, Zn, Fe, FePt, and the like.

While any known method can be used to create nanocrystal phosphors, suitably, a solution-phase colloidal method for controlled growth of inorganic nanomaterial phosphors is used. See Alivisatos, A. P., "Semiconductor clusters, nanocrystals, and quantum dots," Science 271:933 (1996); X. Peng, M. Schlamp, A. Kadavanich, A. P. Alivisatos, "Epitaxial growth of highly luminescent CdSe/CdS Core/Shell nanocrystals with photostability and electronic accessibility," J. Am. Chem. Soc. 30:7019-7029 (1997); and C. B. Murray, D. J. Norris, M. G. Bawendi, "Synthesis and characterization of nearly monodisperse CdE (E=sulfur, selenium, tellurium) semiconductor nanocrystallites," J. Am. Chem. Soc. 115:8706 (1993). This manufacturing process technology leverages low cost proccessability without the need for clean rooms and expensive manufacturing equipment. In these methods, metal precursors that undergo pyrolysis at high temperature are rapidly injected into a hot solution of organic surfactant molecules. These precursors break apart at elevated temperatures and react to nucleate nanocrystals. After this initial nucleation phase, a growth phase begins by the addition of monomers to the growing crystal. The result is freestanding crystalline nanoparticles in solution that have an organic surfactant molecule coating their surface.

Utilizing this approach, synthesis occurs as an initial nucleation event that takes place over seconds, followed by crystal growth at elevated temperature for several minutes. Parameters such as the temperature, types of surfactants present, precursor materials, and ratios of surfactants to monomers can be modified so as to change the nature and progress of the reaction. The temperature controls the structural phase of the nucleation event, rate of decomposition of precursors, and rate of growth. The organic surfactant molecules mediate both solubility and control of the nanocrystal shape.

In semiconductor nanocrystals, photo-induced emission arises from the band edge states of the nanocrystal. The band-edge emission from nanocrystals competes with radiative and non-radiative decay channels originating from surface electronic states. X. Peng, et al., J. Am. Chem. Soc. 30:7019-7029 (1997). As a result, the presence of surface defects such as dangling bonds provide non-radiative recombination centers and contribute to lowered emission efficiency. An efficient and permanent method to passivate and remove the surface trap states is to epitaxially grow an inorganic shell material on the surface of the nanocrystal. X. Peng, et al., J. Am. Chem. Soc. 30:7019-7029 (1997). The shell material can be chosen such that the electronic levels are type I with respect to the core material (e.g., with a larger bandgap to provide a potential step localizing the electron and hole to the core). As a result, the probability of non-radiative recombination can be reduced.

Core-shell structures are obtained by adding organometallic precursors containing the shell materials to a reaction mixture containing the core nanocrystal. In this case, rather than a nucleation-event followed by growth, the cores act as the nuclei, and the shells grow from their surface. The temperature of the reaction is kept low to favor the addition of shell material monomers to the core surface, while preventing independent nucleation of nanocrystals of the shell materials. Surfactants in the reaction mixture are present to direct the controlled growth of shell material and ensure solubility. A uniform and epitaxially grown shell is obtained when there is a low lattice mismatch between the two materials. Additionally, the spherical shape acts to minimize interfacial strain energy from the large radius of curvature, thereby preventing the formation of dislocations that could degrade the optical properties of the nanocrystal system.

In suitable embodiments, ZnS can be used as the shell material using known synthetic processes, resulting in a high-quality emission. As above, if necessary, this material can be easily substituted, e.g., if the core material is modified. Additional exemplary core and shell materials are described herein and/or known in the art.

For many applications of quantum dots, two factors are typically considered in selecting a material. The first factor is the ability to absorb and emit visible light. This consideration makes InP a highly desirable base material. The second factor is the material's photoluminescence efficiency (quantum yield). Generally, Group 12-16 quantum dots (such as cadmium selenide) have higher quantum yield than Group 13-15 quantum dots (such as InP). The quantum yield of InP cores produced previously has been very low (<1%), and therefore the production of a core/shell structure with InP as the core and another semiconductor compound with higher bandgap (e.g., ZnS) as the shell has been pursued in attempts to improve the quantum yield.

Thus, the fluorescent semiconductor nanoparticles (i.e., quantum dots) of the present disclosure include a core and a shell at least partially surrounding the core. The core/shell nanoparticles can have two distinct layers, a semiconductor or metallic core and a shell surrounding the core of an insulating or semiconductor material. The core often contains a first semiconductor material and the shell often contains a second semiconductor material that is different than the first semiconductor material. For example, a first Group 12-16 (e.g., CdSe) semiconductor material can be present in the core and a second Group 12-16 (e.g., ZnS) semiconductor material can be present in the shell.

In certain embodiments of the present disclosure, the core includes a metal phosphide (e.g., indium phosphide (InP), gallium phosphide (GaP), aluminum phosphide (AlP)), a metal selenide (e.g., cadmium selenide (CdSe), zinc selenide (ZnSe), magnesium selenide (MgSe)), or a metal telluride (e.g., cadmium telluride (CdTe), zinc telluride (ZnTe)). In certain embodiments, the core includes a metal phosphide (e.g., indium phosphide) or a metal selenide (e.g., cadmium selenide). In certain preferred embodiments of the present disclosure, the core includes a metal phosphide (e.g., indium phosphide).

The shell can be a single layer or multilayered. In some embodiments, the shell is a multilayered shell. The shell can include any of the core materials described herein. In certain embodiments, the shell material can be a semiconductor material having a higher bandgap energy than the semiconductor core. In other embodiments, suitable shell materials can have good conduction and valence band offset with respect to the semiconductor core, and in some embodiments, the conduction band can be higher and the valence band can be lower than those of the core. In some embodiments, the shell comprises a magnesium or zinc-containing compound. For example, in certain embodiments, semiconductor cores that emit energy in the visible region such as, for example, CdS, CdSe, CdTe, ZnSe, ZnTe, GaP, InP, or GaAs, or near IR region such as, for example, InP, InAs, InSb, PbS, or PbSe may be coated with a shell material having a bandgap energy in the ultraviolet regions such as, for example, ZnS, GaN, and magnesium chalcogenides such as MgS, MgSe, and MgTe. In other embodiments, semiconductor cores that emit in the near IR region can be coated with a material having a bandgap energy in the visible region such as CdS or ZnSe.

Formation of the core/shell nanoparticles may be carried out by a variety of methods. Suitable core and shell precursors useful for preparing semiconductor cores are known in the art and can include Group 2 elements, Group 12 elements, Group 13 elements, Group 14 elements, Group 15 elements, Group 16 elements, and salt forms thereof. For example, a first precursor may include metal salt (M+X−) including a metal atom (M+) such as, for example, Zn, Cd, Hg, Mg, Ca, Sr, Ba, Ga, In, Al, Pb, Ge, Si, or in salts and a counter ion (X−), or organometallic species such as, for example, dialkyl metal complexes. The preparation of a coated semiconductor nanocrystal core and core/shell nanocrystals can be found in, for example, Dabbousi et al. (1997) *J. Phys. Chem. B* 101:9463, Hines et al. (1996) *J. Phys. Chem.* 100: 468-471, and Peng et al. (1997) *J. Amer. Chem. Soc.* 119:7019-7029, as well as in U.S. Pat. No. 8,283,412 (Liu et al.) and International Publication No. WO 2010/039897 (Tulsky et al.).

In certain preferred embodiments of the present disclosure, the shell includes a metal sulfide (e.g., zinc sulfide or cadmium sulfide). In certain embodiments, the shell includes a zinc-containing compound (e.g., zinc sulfide or zinc selenide). In certain embodiments, a multilayered shell includes an inner shell overcoating the core, wherein the inner shell includes zinc selenide and zinc sulfide. In certain embodiments, a multilayered shell includes an outer shell overcoating the inner shell, wherein the outer shell includes zinc sulfide of magnesium sulfide.

In some embodiments, the core of the shell/core nanoparticle contains a metal phosphide such as indium phosphide, gallium phosphide, or aluminum phosphide. The shell contains zinc sulfide, zinc selenide, or a combination thereof. In some more particular embodiments, the core contains indium phosphide and the shell is multilayered with the inner shell containing both zinc selenide and zinc sulfide and the outer shell containing zinc sulfide.

The thickness of the shell(s) may vary among embodiments and can affect fluorescence wavelength, quantum yield, fluorescence stability, and other photostability characteristics of the nanocrystal. The skilled artisan can select the appropriate thickness to achieve desired properties and may modify the method of making the core/shell nanoparticles to achieve the appropriate thickness of the shell(s).

The diameter of the fluorescent semiconductor nanoparticles (i.e., quantum dots) of the present disclosure can affect the fluorescence wavelength. The diameter of the quantum dot is often directly related to the fluorescence wavelength. For example, cadmium selenide quantum dots having an average particle diameter of about 2 to 3 nanometers tend to fluoresce in the blue or green regions of the visible spectrum while cadmium selenide quantum dots having an average particle diameter of about 8 to 10 nanometers tend to fluoresce in the red region of the visible spectrum.

Since carboxylic acids are often used as surfactants in the synthesis of InP/ZnS core/shell particles, the quantum dots may have acid functional ligands attached thereto, prior to dispersing in the stabilizing agent. Similarly, CdSe quantum dots may be functionalized with amine-functional ligands as result of their preparation, prior to functionalization with the instant ligands. As result, the quantum dots may be functionalized with those surface modifying additives or ligands resulting from the original synthesis of the nanoparticles.

As result, the quantum dots may be surface modified with ligands of Formula III:

wherein
$R^5$ is (hetero)hydrocarbyl group having $C_2$ to $C_{30}$ carbon atoms;
$R^{12}$ is a hydrocarbyl group including alkylene, arylene, alkarylene and aralkylene;
n is at least one;
X is a ligand group, including —$CO_2H$, —$SO_3H$, —$P(O)(OH)_2$, —$OP(O)(OH)$, —$OH$ and —$NH_2$.

In addition to, or in lieu of, the ligands of Formula III, the nanoparticles may be surface modified with fluorochemical ligands of the formula:

wherein
$R_f^1$ is a perfluoroalkyl, perfluoroether or perfluoropolyether group of valence w,
$R^2$ is a hydrocarbyl group including alkylene, arylene, alkarylene and aralkylene;
$R^3$ is a hydrocarbyl group including alkylene, arylene, alkarylene and aralkylene;
$X^1$ is —$CH_2$—$O$—, —$O$—, —$S$—, —$CO_2$—, —$CONR^1$—, or —$SO_2NR^{1-}$ where $R^1$ is H or $C_1$-$C_4$ alkyl;
$X^2$ is a covalent bond, —$S$—, —$O$— or —$NR^1$—, —$CO_2$—, —$CONR^1$—, or —$SO_2NR^{1-}$ where $R^1$ is H or $C_1$-$C_4$ alkyl;
v at least one;
w is 1 or 2;
L is an ligand group selected from —$CO_2H$, —$SH$, —$P(O)(OH)_2$, —$P(O)OH$, —$NH_2$—$OH$, and —$SO_3H$. Such fluorochemical ligands are described in Applicant's copending application U.S. 62/269,711, filed 18 Dec. 2015 and incorporated herein by reference.

Such additional surface modifying ligands may be added when the functionalizing with the stabilizing agent of Formula I, or may be attached to the nanoparticles as result of the synthesis. Such additional surface modifying agents are present in amounts less than or equal to the weight of the instant stabilizing copolymer, preferably 10 wt. % or less, relative to the amount of the stabilizing agent.

Various methods can be used to surface modify the fluorescent semiconductor nanoparticles with the ligand compounds. In some embodiments, procedures similar to those described in U.S. Pat. No. 7,160,613 (Bawendi et al.) and U.S. Pat. No. 8,283,412 (Liu et al.) can be used to add the surface modifying agent. For example, the ligand compound and the fluorescent semiconductor nanoparticles can be heated at an elevated temperature (e.g., at least 50° C., at least 60° C., at least 80° C., or at least 90° C.) for an extended period of time (e.g., at least 1 hour, at least 5 hours, at least 10 hours, at least 15 hours, or at least 20 hours).

If desired, any by-product of the synthesis process or any solvent used in surface-modification process can be removed, for example, by distillation, rotary evaporation, or by precipitation of the nanoparticles and centrifugation of the mixture followed by decanting the liquid and leaving behind the surface-modified nanoparticles. In some embodiments, the surface-modified fluorescent semiconductor nanoparticles are dried to a powder after surface-modification. In other embodiments, the solvent used for the surface modification is compatible (i.e., miscible) with any carrier fluids used in compositions in which the nanoparticles are included. In these embodiments, at least a portion of the solvent used for the surface-modification reaction can be included in the carrier fluid in which the surface-modified, fluorescent semiconductor nanoparticles are dispersed.

The fluorescent semiconductor nanoparticles are stabilized using a stabilizing agent having 1) phosphine, stibine or arsine groups and 2) perfluoropolyether groups. The stabilizing agent improves the stability of the quantum dots for their use in quantum dot articles. In particular, the instant stabilizing agent renders the quantum dots stable in the dispersion of secondary fluorochemical carrier fluids, droplets of which are dispersed in the polymeric matrix. The combination of the stabilizing agents with the quantum dots may prevent the quantum dot particles from photodegradation.

More particularly, the stabilizing agent is of the formula:

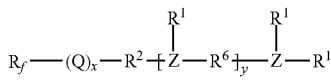

I wherein each $R^1$ is a hydrocarbyl group including alkyl, aryl, alkaryl and aralkyl;
$R^2$ is a divalent hydrocarbyl group selected from alkylene, arylene, alkarylene and aralkylene;
Z is P, As or Sb;
Q is —$CH_2$—S—, —$CH_2$—O—, —$CO_2$—, —$CONR^3$—, —$CH_2$—O—CO—, —NH—CO—$NR^3$—, and —$NR^3$—, where $R^3$ is H or $C_1$-$C_4$ alkyl, and subscript x is 1,
$R^6$ is a divalent hydrocarbyl group selected from alkylene, arylene, alkarylene and aralkylene,
subscript y is 0 or 1, and
$R_f$ is a perfluoropolyether group.

Preferably at least one of the $R^1$ groups is an aryl group, and all of the $R^1$ groups are aryl groups. In some preferred embodiments, at least one of said $R^1$ groups is an aryl or alkaryl group or two of said $R^1$ groups are an aryl or alkaryl group. In some preferred embodiments, $R^1$ is phenyl. In some preferred embodiments $R^2$ comprises are aryl group, an alkaryl group or an aralkyl group. In some preferred embodiments, $R^2$ is phenylene.

The perfluorinated $R_f$ group may be a perfluoroether, or a perfluoropolyether. The $R_f$ groups can be linear, branched and are of the formula:

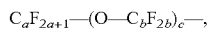

where a is at least 1, preferably 1-10, more preferably 2-6; b is at least 1, preferably 1-10, more preferably 2-6, and c may be a number from 1 to 50, preferably 1 to 30, more preferably 1 to 10.

Exemplary perfluoropolyethers include, but are not limited to, those that have perfluorinated repeating units selected from the group of —($C_pF_{2p}$)—, —($C_pF_{2p}$O)—, —(CF($R_f^2$))—, —(CF($R_f^2$)O)—, —(CF($R_f^2$)$C_pF_{2p}$O)—, —($C_pF_{2p}$CF($R_f^2$)O)—, —($CF_2$CF($R_f^2$)O)—, or combinations thereof. In these repeating units, p is typically an integer of 1 to 10. In some embodiments, p is an integer of 1 to 8, 1 to 6, 1 to 4, 1 to 3, or 1 to 2. The group $R_f^2$ is a fluorine atom, perfluoroalkyl group, perfluoroether group, nitrogen-containing perfluoroalkyl group, perfluoropolyether, or a perfluoroalkoxy group, all of which can be linear, branched, or cyclic. The $R_f^2$ group typically has no more than 12 carbon atoms, no more than 10 carbon atoms, or no more than 9 carbon atoms, no more than 4 carbon atoms, no more than 3 carbon atoms, no more than 2 carbon atoms, or no more than 1 carbon atom. In some embodiments, the $R_f^2$ group can have no more than 4, no more than 3, no more than 2, no more than 1, or no oxygen atoms. In these perfluoropolyether structures, the different repeat units can be distributed randomly along the chain.

Suitable structures for $R_f$ groups include, but are not limited to, $R_f'$—$CF_2O(CF_2O)_q(C_2F_4O)_rCF_2$—, $R_f'$—$(CF_2)_3O(C_4F_8O)_r(CF_2)_3$—, $R_f'$—$CF_2O(C_2F_4O)_rCF_2$—, and $R_f'$—$CF(CF_3)(OCF_2CF(CF_3))_sOC_tF_{2t}O(CF(CF_3)CF_2O)_sCF(CF_3)$—, wherein $R_f'$ is F or a perfluoroalkyl group; q has an average value of 0 to 50, 1 to 50, 3 to 30, 3 to 15, or 3 to 10; r has an average value of 0 to 50, 3 to 30, 3 to 15, or 3 to 10; s has an average value of 0 to 50, 1 to 50, 3 to 30, 3 to 15, or 3 to 10; the sum (r+s) has an average value of 1 to 50 or 4 to 40; the sum (q+r) is greater than 0; and t is an integer of 2 to 6.

As synthesized, compounds typically include a mixture of $R_f$ groups. The average structure is the structure averaged over the mixture components. The values of q, r, and s in these average structures can vary, as long as the compound has a number average molecular weight of at least about 300. Useful compounds often have a molecular weight (number average) of 400 to 5000, 800 to 4000, or 1000 to 5000.

Preferably, $R_f$ is the oligomer of hexafluoropropylene oxide (HFPO) with a number average molecular weight at least 1,000.

The fluorochemical stabilizing agent may be prepared from a perfluoro(poly)ether ester, such as $R_f$—$CO_2CH_3$. The ester can be reacted with an amine or hydroxyl functional compound to provide the stabilizing agents of Formula I, where Q is an ester, thioester or amide. The group is represented by Z*

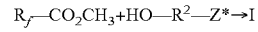

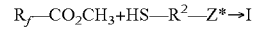

Alternatively, the ester can be reacted with an olefin having nucleophilic groups, such as an amine (or a thiol), and the resulting compound optionally functionalized by an ene reaction, such as with mercaptosuccinic acid.

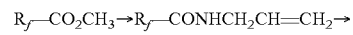

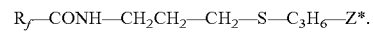

An ester of a perfluorinated acid can be reduced to a —$CH_2$—OH group, facilitating preparation of compounds having a —$CH_2$—OH "Q" group. This in turn may be reacted with a halide, such as allyl bromide to provide a terminal allyl unsaturation, which in turn may be functionalized by an ene reaction, as illustrated above. The nucleophilic —$CH_2$—OH terminal group may be reacted with a compound having an electrophilic group to provide the requisite unsaturation.

$R_f$—$CH_2$—OH+E-$R^2$—Z*→I, where E is an electrophilic functional group including carboxylic acids, ester, acid halide, isocyanate, aziridine, and other known in the art.

The —$CH_2$—O-Q group can be converted to a —$CH_2$—S— group by reacting with a perfluorosulfonyl fluoride, displacement with a thioester, followed by hydrolysis. The —$CH_2$—SH may be used in displacement and condensation reaction, or in ene reactions to provide the requisite Z* group. Longer chain thiols may be prepared by reacting compounds of the formula $R_f$—$CH_2$OH with an allyl halide to provide a terminal allyl group, followed by an ene reaction with a thioester, and hydrolysis.

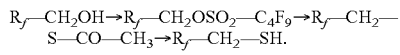

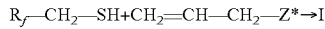

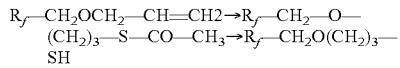

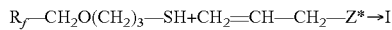

Alternatively, a perfluorinated acid fluoride may be reacted with fluoride ion to produce an intermediate having a nucleophilic —$CF_2$—$O^-$ group as shown. Similarly, perfluoroketones may be reacted with fluoride ion to produce a secondary perfluoroalkoxide nucleophile. The intermediate may be reacted with a compound of the formula Y—$R^2$—Z*, where Y is a leaving group, such as halide or tosylate:

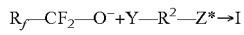

A dispersion of the fluorochemical stabilized nanoparticles composition (using compounds of Formula I) may also include a secondary fluorinated carrier fluid. Preferably the dispersion comprises a secondary fluorinated carrier fluid. The secondary fluorinated carrier fluid are typically selected to be compatible (i.e., miscible) with the stabilizing agent of Formula I added to the fluorescent semiconductor nanoparticles. The stabilized nanoparticles and secondary fluorinated carrier fluid form a coating that is transparent when viewed with the human eye. Likewise, any precursors of the polymeric materials that are included in the dispersion composition are soluble in a secondary fluorinated carrier fluid and form a coating that is transparent when viewed with the unaided human eye. The term transparent means transmitting at least 85% of incident light in the visible spectrum (about 400-700 nm wavelength).

The optional secondary fluorinated carrier fluids are inert, liquid at 25° C. and have a boiling point ≥100° C., preferably ≥150° C.; and can be one or a mixture of perfluorinated or highly fluorinated liquid compounds having, in some embodiments, at least 8 carbon atoms or more, and optionally containing one or more catenary heteroatoms, such as divalent oxygen, hexavalent sulfur, or trivalent nitrogen and having a hydrogen content of less than 5 percent by weight or less than 1 percent by weight. Higher boiling points are preferred so that the carrier fluids remain when organic solvents used in the preparation are removed.

Suitable fluorinated, inert secondary carrier fluids include perfluoroalkanes or perfluorocycloalkanes, such as, perfluorooctane, perfluorononane, perfluorodecane, perfluorotetradecahydrophenanthrene, perfluorodecalin, and perfluoromethyldecalin; perfluoroamines, such as, perfluorotripentyl amine, perfluorotributyl amine, perfluorotripropyl amine, perfluorotriamyl amine, and perfluoro-N-isopropyl morpholine; perfluoroethers, such as $HCF_2(OCF(CF_3)CF_2)_s OCF_2CF_2H$, $HCF_2(OCF(CF_3)CF_2)_s$—$(OCF_2)_q$—$OCF_2H$, (where subscripts s and q are as defined for the fluorinated ligand compounds), perfluorobutyl tetrahydrofuran, perfluorodibutyl ether, perfluorobutoxyethoxy formal, perfluorohexyl formal, and perfluorooctyl formal; perfluoropolyethers; hydrofluorocarbons, such as pentadecafluorohydroheptane, 1,1,2,2-tetrafluorocyclobutane, 1-trifluoromethyl-1,2,2-trifluorocyclobutane and 2-hydro-3-oxaheptadecafluorooctane.

In some embodiments, the quantum dots stabilized by the compounds of Formula I are added to the secondary fluorinated carrier fluid in amounts such that the optical density is at least 10, optical density defined as the absorbance at 440 nm for a cell with a path length of 1 cm) solution.

Binder

The stabilized fluorescent semiconductor nanoparticles may be dispersed in a solution, suspension or dispersion that contains (a) a fluorinated carrier fluid and (b) a polymeric binder, a precursor of the polymeric binder, or combinations thereof. The stabilized nanoparticles may be dispersed in the secondary fluorochemical carrier fluid, which is then dispersed in the polymeric binder, forming droplets of the nanoparticles in the secondary carrier fluid, which in turn are dispersed in the polymeric binder.

The polymeric binders desirably provide barrier properties to exclude oxygen and moisture. If water and/or oxygen enter the quantum dot article, the quantum dots can degrade and ultimately fail to emit light when excited by ultraviolet or blue light irradiation. Slowing or eliminating quantum dot degradation along the laminate edges is particularly important to extend the service life of the displays in smaller electronic devices such as those utilized in, for example, handheld devices and tablets.

The polymeric binders or resins desirably provide barrier properties to exclude oxygen and moisture when cured. If water and/or oxygen enter the quantum dot article, the quantum dots can degrade and ultimately fail to emit light when excited by ultraviolet or blue light irradiation. Slowing or eliminating quantum dot degradation along the laminate edges is particularly important to extend the service life of the displays in smaller electronic devices such as those utilized in, for example, handheld devices and tablets.

Exemplary polymeric binders include, but are not limited to, polysiloxanes, fluoroelastomers, polyamides, polyimides, polycarolactones, polycaprolactams, polyurethanes, polyvinyl alcohols, polyvinyl chlorides, polyvinyl acetates, polyesters, polycarbonates, polyacrylates, polymethacrylates, polyacrylamides, and polymethacrylamides.

Suitable precursors of the polymeric binder or resin include any precursor materials used to prepare the polymeric materials listed above. Exemplary precursor materials include acrylates that can be polymerized to polyacrylates, methacrylates that can be polymerized to form polymethacrylates, acrylamides that can be polymerized to form polyacrylamides, methacrylamides that can be polymerized to form polymethacrylamides, epoxy resins and dicarboxylic acids that can be polymerized to form polyesters, diepoxides that can be polymerized to form polyethers, isocyanates and polyols that can be polymerized to form polyurethanes, or polyols and dicarboxylic acids that can be polymerized to form polyesters.

In some embodiments, such as CdSe, the polymeric binder is a thermally curable epoxy-amine composition optionally further comprising a radiation-curable acrylate as described in Applicant's copending WO 2015/095296 (Eckert et al.); Thiol-epoxy resins as described in U.S. 62/148,209 (Qiu et al., filed 16 Apr. 2015), thiol-alkene-epoxy resins as described in U.S. 62/148,212 (Qui et al. filed 16 Apr. 2015); thiol-alkene resins as described in U.S. 62/080,488 (Qui et al., filed 17 Nov. 2014), and thiol silicones as described in WO 2015/138174 (Qiu et al., published 17 Sep. 2015).

In some preferred embodiments the polymeric binder is a radiation curable oligomer having the general formula

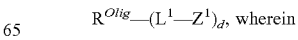

$R^{Olig}$ groups include urethanes, polyurethanes, esters, polyesters, polyethers, polyolefins, polybutadienes and epoxies;

L¹ is a linking group;

Z¹ is a pendent, free-radically polymerizable group such as (meth)acryloyl, vinyl or alkynyl and is preferably a (meth)acrylate, and d is greater than 1, preferably at least 2.

The linking group L¹ between the oligomer segment and ethylenically unsaturated end group includes a divalent or higher valency group selected from an alkylene, arylene, heteroalkylene, or combinations thereof and an optional divalent group selected from carbonyl, ester, amide, sulfonamide, or combinations thereof. L¹ can be unsubstituted or substituted with an alkyl, aryl, halo, or combinations thereof. The L¹ group typically has no more than 30 carbon atoms. In some compounds, the L¹ group has no more than 20 carbon atoms, no more than 10 carbon atoms, no more than 6 carbon atoms, or no more than 4 carbon atoms. For example, L¹ can be an alkylene, an alkylene substituted with an aryl group, or an alkylene in combination with an arylene or an alkyl ether or alkyl thioether linking group.

The pendent, free radically polymerizable functional groups Z¹ may be selected from the group consisting of vinyl, vinyl ether, ethynyl, and (meth)acyroyl which includes acrylate, methacrylate, acrylamide and methacrylamide groups.

The oligomeric group $R^{olig}$ may be selected from poly(meth)acrylate, polyurethane, polyepoxide, polyester, polyether, polysulfide, polybutadiene, hydrogenated polyolefins (including hydrogenated polybutadienes, isoprenes and ethylene/propylene copolymers, and polycarbonate oligomeric chains.

As used herein, "(meth)acrylated oligomer" means a polymer molecule having at least two pendent (meth)acryloyl groups and a weight average molecular weight ($M_w$) as determined by Gel Permeation Chromatography of at least 1,000 g/mole and typically less than 50,000 g/mole.

(Meth)acryloyl epoxy oligomers are multifunctional (meth)acrylate esters and amides of epoxy resins, such as the (meth)acrylated esters of bisphenol-A epoxy resin. Examples of commercially available (meth)acrylated epoxies include those known by the trade designations EBECRYL 600 (bisphenol A epoxy diacrylate of 525 molecular weight), EBECRYL 605 (EBECRYL 600 with 25% tripropylene glycol diacrylate), EBECRYL 3700 (bisphenol-A diacrylate of 524 molecular weight) and EBECRYL 3720H (bisphenol A diacrylate of 524 molecular weight with 20% hexanediol diacrylate) available from Cytec Industries, Inc., Woodland Park, N.J.; and PHOTOMER 3016 (bisphenol A epoxy acrylate), PHOTOMER 3016-40R (epoxy acrylate and 40% tripropylene glycol diacrylate blend), and PHOTOMER 3072 (modified bisphenol A acrylate, etc.) available from BASF Corp., Cincinnati, Ohio, and Ebecryl 3708 (modified bisphenol A epoxy diacrylate) available from Cytec Industries, Inc., Woodland Park, N.J.

(Meth)acrylated urethanes are multifunctional (meth)acrylate esters of hydroxy terminated isocyanate extended polyols, polyesters or polyethers. (Meth)acrylated urethane oligomers can be synthesized, for example, by reacting a diisocyanate or other polyvalent isocyanate compound with a polyvalent polyol (including polyether and polyester polyols) to yield an isocyanate terminated urethane prepolymer. A polyester polyol can be formed by reacting a polybasic acid (e.g., terephthalic acid or maleic acid) with a polyhydric alcohol (e.g., ethylene glycol or 1,6-hexanediol). A polyether polyol useful for making the acrylate functionalized urethane oligomer can be chosen from, for example, polyethylene glycol, polypropylene glycol, poly(tetrahydrofuran), poly(2-methyl-tetrahydrofuran), poly(3-methyl-tetrahydrofuran) and the like. Alternatively, the polyol linkage of an acrylated urethane oligomer can be a polycarbonate polyol.

Subsequently, (meth)acrylates having a hydroxyl group can then be reacted with the terminal isocyanate groups of the prepolymer. Both aromatic and the preferred aliphatic isocyanates can be used to react with the urethane to obtain the oligomer. Examples of diisocyanates useful for making the (meth)acrylated oligomers are 2,4-tolylene diisocyanate, 2,6-tolylene diisocyanate, 1,3-xylylene diisocyanate, 1,4-xylylene diisocyanate, 1,6-hexane diisocyanate, isophorone diisocyanate and the like. Examples of hydroxy terminated acrylates useful for making the acrylated oligomers include, but are not limited to, 2-hydroxyethyl (meth)acrylate, 2-hydroxypropyl (meth)acrylate, α-hydroxybutyl acrylate, polyethylene glycol (meth)acrylate and the like.

A (meth)acrylated urethane oligomer can be, for example, any urethane oligomer having at least two acrylate functionalities and generally less than about six functionalities. Suitable (meth)acrylated urethane oligomers are also commercially available such as, for example, those known by the trade designations PHOTOMER 6008, 6019, 6184 (aliphatic urethane triacrylates) available from Henkel Corp.; EBECRYL 220 (hexafunctional aromatic urethane acrylate of 1000 molecular weight), EBECRYL 284 (aliphatic urethane diacrylate of 1200 molecular weight diluted with 12% of 1,6-hexanediol diacrylate), EBECRYL 4830 (aliphatic urethane diacrylate of 1200 molecular weight diluted with 10% of tetraethylene glycol diacrylate), and EBECRYL 6602 (trifunctional aromatic urethane acrylate of 1300 molecular weight diluted with 40% of trimethylolpropane ethoxy triacrylate), available from UCB Chemical; and SARTOMER CN1963, 963E75, 945A60, 963B80, 968, and 983) available from Sartomer Co., Exton, Pa.

Properties of these materials may be varied depending upon selection of the type of isocyanate, the type of polyol modifier, the reactive functionality and molecular weight. Diisocyanates are widely used in urethane acrylate synthesis and can be divided into aromatic and aliphatic diisocyanates. Aromatic diisocyanates are used for manufacture of aromatic urethane acrylates which have significantly lower cost than aliphatic urethane acrylates but tend to noticeably yellow on white or light colored substrates. Aliphatic urethane acrylates include aliphatic diisocyanates that exhibit slightly more flexibility than aromatic urethane acrylates that include the same functionality, a similar polyol modifier and at similar molecular weight.

The curable composition may comprise a functionalized poly(meth)acrylate oligomer, which may be obtained from the reaction product of: (a) from 50 to 99 parts by weight of (meth)acrylate ester monomer units that are homo- or co-polymerizable to a polymer (b) from 1 to 50 parts by weight of monomer units having a pendent, free-radically polymerizable functional group. Examples of such materials are available from Lucite International (Cordova, Tenn.) under the trade designations of Elvacite 1010, Elvacite 4026, and Elvacite 4059.

The (meth)acrylated poly(meth)acrylate oligomer may comprise a blend of an acrylic or hydrocarbon polymer with multifunctional (meth)acrylate diluents. Suitable polymer/diluent blends include, for example, commercially available products such as EBECRYL 303, 745 and 1710 all of which are available from Cytec Industries, Inc., Woodland Park, N.J.

The curable composition may comprise a (meth)acrylated polybutadiene oligomer, which may be obtained from a carboxyl- or hydroxyl-functionalized polybutadiene. By carboxyl or hydroxy functionalised polybutadiene is meant to designate a polybutadiene comprising free —OH or —COOH groups. Carboxyl functionalized polybutadienes are known, they have for example been described in U.S. Pat. No. 3,705,208 (Nakamuta et al.) and are commercially available under the trade name of Nisso PB C-1000 (Nisso America, New York, N.Y.). Carboxyl functionalized polybutadienes can also be obtained by the reaction of a hydroxyl functionalized polybutadiene (that is a polybutadiene having free hydroxyl groups) with a cyclic anhydride such as for example has been described in U.S. Pat. No. 5,587,433 (Boeckeler), U.S. Pat. No. 4,857,434 (Klinger) and U.S. Pat. No. 5,462,835 (Mirle).

Carboxyl and hydroxyl functionalized polybutadienes suitable for being used in the process according to the present invention contain besides the carboxyl and/or hydroxyl groups, units derived from the polymerization of butadiene. The polybutadiene (PDB) generally comprises 1-4 cis units/1-4 trans units/1-2 units in a ratio a/b/c where a, b and c range from 0 to 1 with a+b+c=1. The number average molecular weight ($M_n$) of the functionalized polybutadiene is preferably from 200 to 10000 Da. The $M_n$ is more preferably at least 1000. The $M_n$ more preferably does not exceed 5000 Da. The —COOH or —OH functionality is generally from 1.5 to 9, preferably from 1.8 to 6.

Exemplary hydroxyl and carboxyl polybutadienes include without limitation Poly BD R-20LM (hydroxyl functionalized PDB, a=0.2, b=0.6, c=0.2, $M_n$ 1230) and Poly BD R45-HT (hydroxyl functionalized PDB, a=0.2, b=0.6, c=0.2, $M_n$ 2800) commercialized by Atofina, Nisso-PB G-1000 (hydroxyl functionalized PDB, a=0, b<0.15, c>0.85, $M_n$ 1250-1650), Nisso-PB G-2000 (hydroxyl functionalized PDB, a=0, b<0.15, c>0.85, $M_n$ 1800-2200), Nisso-PB G-3000 (hydroxyl functionalized PDB, a=0, b<0.10, c>0.90, $M_n$ 2600-3200), Nisso-PB C-1000 (carboxyl functionalized PDB, a=0, b<0.15, c>0.85, Mn 1200-1550) obtainable from Nisso America, New York, N.Y.

When carboxyl functionalized polybutadienes obtained from the reaction of a hydroxyl functionalized polybutadiene with a cyclic anhydride are used, this cyclic anhydride preferably include phthalic anhydride, hexahydrophthalic anhydride, glutaric anhydride, succinic anhydride, dodecenylsuccinic anhydride, maleic anhydride, trimellitic anhydride, pyromellitic anhydride. Mixtures of anhydrides can also be used. The amount of anhydride used for the preparation of a carboxyl functionalized polybutadiene from a hydroxyl functionalized polybutadiene is generally at least 0.8 molar, preferably at least 0.9 molar and more preferably at least 0.95 molar equivalent per molar equivalents of —OH groups present in the polybutadiene.

A (meth)acrylated polybutadiene oligomer, which is the reaction product of a carboxyl functionalized polybutadiene, may be prepared with a (meth)acrylated monoepoxide. (Meth)acrylated mono-epoxides are known. Examples of (meth)acrylated mono-epoxides that can be used are glycidyl (meth)acrylate esters, such as glycidylacrylate, glycidylmethacrylate, 4-hydroxybutylacrylate glycidylether, bisphenol-A diglycidylether monoacrylate. The (meth)acrylated mono-epoxides are preferably chosen from glycidylacrylate and glycidylmethacrylate. Alternatively, a (meth)acrylated polybutadiene oligomer which is the reaction product of a hydroxyl functionalized polybutadiene may be prepared with a (meth)acrylate ester, or halide.

Some (meth)acrylated polybutadienes that can be used, for example, include Ricacryl 3100 and Ricacryl 3500, manufactured by Sartomer Company, Exton, Pa., USA, and Nisso TE-2000 available from Nisso America, New York, N.Y. Alternatively, other methacrylated polybutadienes can be used. These include dimethacrylates of liquid polybutadiene resins composed of modified, esterified liquid polybutadiene diols. These are available under the tradename CN301 and CN303, and CN307, manufactured by Sartomer Company, Exton, Pa., USA. Regardless which methacrylated polybutadiene is used with embodiments of the invention, the methacrylated polybutadiene can include a number of methacrylate groups per chain from about 2 to about 20.

Alternatively, the acrylate functionalized oligomers can be polyester acrylate oligomers, acrylated acrylic oligomers, acrylated epoxy oligomers, polycarbonate acrylate oligomers or polyether acrylate oligomers. Useful epoxy acrylate oligomers include CN2003B from Sartomer Co. (Exton, Pa.). Useful polyester acrylate oligomers include CN293, CN294, and CN2250, 2281, 2900 from Sartomer Co. (Exton, Pa.) and EBECRYL 80, 657, 830, and 1810 from UCB Chemicals (Smyrna, Ga.). Suitable polyether acrylate oligomers include CN501, 502, and 551 from Sartomer Co. (Exton, Pa.). Useful polycarbonate acrylate oligomers can be prepared according to U.S. Pat. No. 6,451,958 (Sartomer Technology Company Inc., Wilmington, Del.).

In each embodiment comprising a (meth)acrylated oligomer, the curable binder composition optionally, yet preferably, comprises diluent monomer in an amount sufficient to reduce the viscosity of the curable composition such that it may be coated on a substrate. In some embodiments, the composition may comprise up to about 70 wt-% diluent monomers to reduce the viscosity of the oligomeric component to less than 10000 centipoise and to improve the processability.

Useful monomers are desirably soluble or miscible in the (meth)acrylated oligomer, highly polymerizable therewith. Useful diluents are mono- and polyethylenically unsaturated monomers such as (meth)acrylates or (meth)acrylamides. Suitable monomers typically have a number average molecular weight no greater than 450 g/mole. The diluent monomer desirably has minimal absorbance at the wavelength of the radiation used to cure the composition. Such diluent monomers may include, for example, n-butyl acrylate, isobutyl acrylate, hexyl acrylate, 2-ethyl-hexylacrylate, isooctylacrylate, caprolactoneacrylate, isodecylacrylate, tridecylacrylate, laurylmethacrylate, methoxy-polyethyleneglycol-monomethacrylate, laurylacrylate, tetrahydrofurfurylacrylate, ethoxy-ethoxyethyl acrylate and ethoxylatednonylacrylate. Especially preferred are 2-ethylhexylacrylate, ethoxy-ethoxyethyl acrylate, tridecylacrylate and ethoxylated nonylacrylate. High $T_g$ monomers having one ethylenically unsaturated group and a glass transition temperature of the corresponding homopolymer of 50° C. or more which are suitable in the present invention, include, for example, N-vinylpyrrolidone, N-vinyl caprolactam, isobornyl acrylate, acryloylmorpholine, isobornylmethacrylate, phenoxyethylacrylate, phenoxyethylmethacrylate, methylmethacrylate and acrylamide.

Furthermore, the diluent monomers may contain an average of two or more free-radically polymerizable groups. A diluent having three or more of such reactive groups can be present as well. Examples of such monomers include: $C_2$-$C_{18}$ alkylenedioldi(meth)acrylates, $C_3$-$C_{18}$ alkylenetrioltri(meth)acrylates, the polyether analogues thereof, and the like, such as 1,6-hexanedioldi(meth)acrylate, trimethylolpropanetri(meth)acrylate, triethyleneglycoldi(meth)acrylate, pentaeritritoltri(meth)acrylate, and tripropyleneglycol di(meth)acrylate, and di-trimethylolpropane tetraacrylate.

Suitable preferred diluent monomers include for example benzyl (meth)acrylate, phenoxyethyl (meth)acrylate; phenoxy-2-methylethyl (meth)acrylate; phenoxyethoxyethyl (meth)acrylate, 1-naphthyloxy ethyl acrylate; 2-naphthyloxy ethyl acrylate; phenoxy 2-methylethyl acrylate; phenoxyethoxyethyl acrylate; 2-phenylphenoxy ethyl acrylate; 4-phenylphenoxy ethyl acrylate; and phenyl acrylate.

Preferred diluent monomers includes phenoxyethyl (meth)acrylate, benzyl (meth)acrylate, and tricyclodecane dimethanol diacrylate. Phenoxyethyl acrylate is commercially available from Sartomer under the trade designation "SR339"; from Eternal Chemical Co. Ltd. under the trade designation "Etermer 210"; and from Toagosei Co. Ltd under the trade designation "TO-1166". Benzyl acrylate is commercially available from Osaka Organic Chemical, Osaka City, Japan. Tricyclodecane dimethanol diacrylate is commercially available from Sartomer under the trade designation "SR833".

Such optional monomer(s) may be present in the polymerizable composition in amount of at least about 5 wt-%. The optional monomer(s) typically total no more than about 70 wt-% of the curable composition. The some embodiments the total amount of diluent monomer ranges from about 10 wt-% to about 50-%.

When using a free-radically curable polymeric binder, the curable composition further comprises photoinitiators, in an amount between the range of about 0.1% and about 5% by weight.

Useful photoinitiators include those known as useful for photocuring free-radically polyfunctional (meth)acrylates. Exemplary photoinitiators include benzoin and its derivatives such as alpha-methylbenzoin; alpha-phenylbenzoin; alpha-allylbenzoin; alpha-benzylbenzoin; benzoin ethers such as benzil dimethyl ketal (e.g., "IRGACURE 651" from BASF, Florham Park, N.J.), benzoin methyl ether, benzoin ethyl ether, benzoin n-butyl ether; acetophenone and its derivatives such as 2-hydroxy-2-methyl-1-phenyl-1-propanone (e.g., "DAROCUR 1173" from BASF, Florham Park, N.J.) and 1-hydroxycyclohexyl phenyl ketone (e.g., "IRGACURE 184" from BASF, Florham Park, N.J.); 2-methyl-1-[4-(methylthio)phenyl]-2-(4-morpholinyl)-1-propanone (e.g., "IRGACURE 907" from BASF, Florham Park, N.J.); 2-benzyl-2-(dimethylamino)-1-[4-(4-morpholinyl)phenyl]-1-butanone (e.g., "IRGACURE 369" from BASF, Florham Park, N.J.) and phosphine oxide derivatives such as ethyl-2,4,6-trimethylbenzoylphenylphoshinate (e.g. "TPO-L" from BASF, Florham Park, N.J.), and IRGACURE 819 (phenylbis(2,4,6-trimethylbenzoyl)phosphine oxide) available from BASF, Florham Park, N.J.

Other useful photoinitiators include, for example, pivaloin ethyl ether, anisoin ethyl ether, anthraquinones (e.g., anthraquinone, 2-ethylanthraquinone, 1-chloroanthraquinone, 1,4-dimethylanthraquinone, 1-methoxyanthraquinone, or benzanthraquinone), halomethyltriazines, benzophenone and its derivatives, iodonium salts and sulfonium salts, titanium complexes such as bis(etas-2,4-cyclopentadien-1-yl)-bis[2,6-difluoro-3-(1H-pyrrol-1-yl) phenyl]titanium (e.g., "CGI 784DC" from BASF, Florham Park, N.J.); halomethyl-nitrobenzenes (e.g., 4-bromomethylnitrobenzene), mono- and bis-acylphosphines (e.g., "IRGACURE 1700", "IRGACURE 1800", "IRGACURE 1850", and "DAROCUR 4265").

In some embodiments, the polymeric binder is an epoxy compound that can be cured or polymerized by the processes that are those known to undergo cationic polymerization and include 1,2-, 1,3-, and 1,4-cyclic ethers (also designated as 1,2-, 1,3-, and 1,4-epoxides). Suitable epoxy binders can include, for example, those epoxy binders described in U.S. Pat. No. 6,777,460. In particular, cyclic ethers that are useful include the cycloaliphatic epoxies such as cyclohexene oxide and the ERL™ and UVR™ series type of binders available from Dow Chemical, Midland, Mich., such as vinylcyclohexene oxide, vinylcyclohexene dioxide, 3,4-epoxycyclohexylmethyl-3,4-epoxycyclohexane carboxylate, bis-(3,4-epoxycyclohexyl) adipate and 2-(3,4-epoxycyclohexyl-5,5-spiro-3,4-epoxy) cyclohexene-meta-dioxane; also included are the glycidyl ether type epoxy binders such as propylene oxide, epichlorohydrin, styrene oxide, glycidol, the EPON, EPONEX, and HELOXY series type of epoxy binders available from Resolution Performance Products, Houston, Tex., including the diglycidyl either of bisphenol A and chain extended versions of this material such as EPON 828, EPON 1001, EPON 1004, EPON 1007, EPON 1009 and EPON 2002 or their equivalent from other manufacturers, EPONEX 1510, the hydrogenated diglycidyl either of bisphenol A, HELOXY 67, diglycidyl ether of 1,4-butanediol, HELOXY™ 107, diglycidyl ether of cyclohexane dimethanol, or their equivalent from other manufacturers, dicyclopentadiene dioxide, epoxidized vegetable oils such as epoxidized linseed and soybean oils available as VIKOLOX and VIKOFLEX binders from Atofina, Philadelphia, Pa., epoxidized KRATON LIQUID POLYMERS, such as L-207 available from Kraton Polymers, Houston, Tex., epoxidized polybutadienes such as the POLY BD binders from Atofina, Philadelphia, Pa., 1,4-butanediol diglycidyl ether, polyglycidyl ether of phenolformaldehyde, and for example DEN™ epoxidized phenolic novolac binders such as DEN 431 and DEN 438 available from Dow Chemical Co., Midland Mich., epoxidized cresol novolac binders such as ARALDITE ECN 1299 available from Vantico AG, Basel, Switzerland, resorcinol diglycidyl ether, and epoxidized polystyrene/polybutadiene blends such as the Epofriendz binders such as EPOFRIEND A1010 available from Daicel USA Inc., Fort Lee, N.J., and resorcinol diglycidyl ether.

Higher molecular weight polyols include the polyethylene and polypropylene oxide polymers in the molecular weight (Mn) range of 200 to 20,000 such as the CARBOWAX polyethyleneoxide materials available from Dow Chemical Co., Midland, Mich., caprolactone polyols in the molecular weight range of 200 to 5,000 such as the TONE polyol materials available from Dow, polytetramethylene ether glycol in the molecular weight range of 200 to 4,000, such as the TERATHANE materials available from DuPont and POLYTHF 250 from BASF, polyethylene glycol, such as PEG™ 200 available from Dow, hydroxyl-terminated polybutadiene binders such as the POLY BD materials available from Atofina, Philadelphia, Pa., phenoxy binders such as those commercially available from Phenoxy Associates, Rock Hill, S.C., or equivalent materials supplied by other manufacturers.

It is also within the scope of this invention to include one or more epoxy binders which can be blended together. It is also within the scope of this invention to include one or more mono or poly-alcohols which can be blended together. The different kinds of binders and alcohols can be present in any proportion.

It is within the scope of this invention to use vinyl ether monomers as the cationically curable material. Vinyl ether-containing monomers can be methyl vinyl ether, ethyl vinyl ether, tert-butyl vinyl ether, isobutyl vinyl ether, triethyleneglycol divinyl ether (RAPT-CURE DVE-3, available from International Specialty Products, Wayne, N.J.), 1,4-cyclohexanedimethanol divinyl ether (RAPI-CURE CHVE, International Specialty Products), trimetylolpropane trivinyl ether (available from BASF Corp., Mount Olive, N.J.) and the VECTOMER divinyl ether binders from Morflex, Greensboro, N.C., such as VECTOMER 2010, VECTOMER 2020, VECTOMER 4010, and VECTOMER 4020, or their equivalent from other manufacturers. It is within the scope of this invention to use a blend of more than one vinyl ether binder.

It is also within the scope of this invention to use one or more epoxy binders blended with one or more vinyl ether binders. The different kinds of binders can be present in any proportion.

The preferred epoxy binders include the ERL and the UVR type of binders especially 3,4-epoxycyclohexylmethyl-3,4-epoxycyclohexanecarboxylate, bis-(3,4-epoxycyclohexyl) adipate and 2-(3,4-epoxycylclohexyl-5,5-spiro-3,4-epoxy) cyclohexene-meta-dioxane and the bisphenol A EPON type binders including 2,2-bis-p-(2,3-epoxypropoxy) phenylpropane and chain extended versions of this material and, binders of the type EPONEX 1510 and HELOXY 107 and 68. Also useful in the present invention are purified versions of these epoxies as described in U. S. Published Patent Application 2002/0022709 published 21 Feb. 2002.

When preparing compositions containing epoxy monomers, hydroxy-functional materials can be added. The hydroxyl-functional component can be present as a mixture or a blend of materials and can contain mono- and polyhydroxyl containing materials. Preferably, the hydroxy-functional material is at least a diol. When used, the hydroxyl-functional material can aid in chain extension and in preventing excess crosslinking of the epoxy during curing, e. g., increasing the toughness of the cured composition.

When present, useful hydroxyl-functional materials include aliphatic, cycloaliphatic or alkanol-substituted arene mono- or poly-alcohols having from about 2 to about 18 carbon atoms and two to five, preferably two to four hydroxy groups, or combinations thereof. Useful mono-alcohols can include methanol, ethanol, 1-propanol, 2-propanol, 2-methyl-2-propanol, 1-butanol, 2-butanol, 1-pentanol, neopentyl alcohol, 3-pentanol, 1-hexanol, 1-heptanol, 1-octanol, 2-phenoxyethanol, cyclopentanol, cyclohexanol, cyclohexylmethanol, 3-cyclohexyl-1-propanol, 2-norbornanemethanol and tetrahydrofurfuryl alcohol.

Polyols useful in the present invention include aliphatic, cycloaliphatic, or alkanol-substituted arene polyols, or mixtures thereof having from about 2 to about 18 carbon atoms and two to five, preferably two to four hydroxyl groups. Examples of useful polyols include 1,2-ethanediol, 1,2-propanediol, 1,3-propanediol, 1,4-butanediol, 1,3-butanediol, 2-methyl-1,3-propanediol, 2,2-dimethyl-1, 3-propanediol, 2-ethyl-1,6-hexanediol, 1,5-pentanediol, 1,6-hexanediol, 1,8-octanediol, neopentyl glycol, glycerol, trimethylolpropane, 1,2,6-hexanetriol, trimethylolethane, pentaerythritol, quinitol, mannitol, sorbitol, diethylene glycol, triethylene glycol, tetraethylene glycol, glycerine, 2-ethyl-2-(hydroxymethyl)-1,3-propanediol, 2-ethyl-1,3-pentanediol, 1,4-cyclohexanedimethanol, 1,4-benzene-dimethanol and polyalkoxylated bisphenol A derivatives. Other examples of useful polyols are disclosed in U.S. Pat. No. 4,503,211.

Bi-functional monomers having both cationically polymerizable and free-radically polymerizable moieties in the same monomer are useful in the present invention, such as, for example, glycidyl methacrylate, or 2-hydroxyethyl acrylate.

It is also within the scope of this invention to add a free radically polymerizable monomer, such as an acrylate or methacrylate. The addition of such a monomer broadens the scope of obtainable physical properties and processing options. When two or more polymerizable monomers are present, they can be present in any proportion.

Suitable cationic photoinitiators are selected from organic onium cations, for example those described in photoinitiators for Free Radical Cationic & Anionic Photopolymerization, 2'-d Edition, J. V. Crivello & K. Dietliker, John Wiley and Sons, 1998, pp. 275 to 298, and U.S. Pat. Nos. 4,250, 311, 3,708,296, 4,069,055, 4,216,288, 5,084,586 and 5,124, 417 and such descriptions incorporated herein by reference, including aliphatic or aromatic Group IVA-VIIA (CAS version) centered onium salts, preferably I-, S-, P- and C-centered onium salts, such as those selected from sulfoxonium, diaryliodonium, triarylsulfonium, carbonium and phosphonium, and most preferably I-, and S-centered onium salts, such as those selected from sulfoxonium, diaryliodonium, and triarylsulfonium, wherein "aryl" means an unsubstituted or substituted aromatic moiety having up to four independently selected substituents.

In some embodiments, the polymeric binder is a thermally curable epoxy-amine composition optionally further comprising a radiation-curable acrylate as described in Applicant's copending WO 2015095296 (Eckert et al.); Thiol-epoxy resins as described in U.S. 62/148,209 (Qiu et al., filed 16 Apr. 2015), thiol-alkene-epoxy resins as described in U.S. 62/148,212 (Qui et al. filed 16 Apr. 2015); thiol-alkene resins as described in U.S. 62/080,488 (Qui et al., filed 17 Nov. 2014), and thiol silicones as described in WO 2015/138174 (Qiu et al., published 17 Sep. 2015).

The quantum dot layer can have any useful amount of quantum dots, and in some embodiments the quantum dot layer can include from 0.1 to 10 wt %, preferably 0.1 to 1 wt %, quantum dots, based on the total weight of the quantum dot layer (dots, optional liquid carrier and polymeric binder). The dispersion composition can also contain a surfactant (i.e., leveling agent), a polymerization initiator, and other additives, as known in the art.

Generally, the stabilized quantum dots, the surface modifying ligand, the polymeric binder and optional fluorinated carrier fluid are combined and subject to high shear mixing to produce a dispersion of the ligand functional quantum dots in the polymer matrix. The matrix is chosen such there is limited compatibility and the quantum dots form a separate, non-aggregating phase in the matrix. As the quantum dots are often prepared and ligand-functionalized in an organic solvent, the fluorinated carrier fluid enables separation and removal of any organic solvent.

The dispersion, comprising droplets of stabilized nanoparticle and optional fluorochemical carrier fluid, are dispersed in the binder resin, is then coated and cured either thermally, free-radically, or both to lock in the dispersed structure and exclude oxygen and water from the dispersed quantum dots.

When using a free-radically curable polymeric binder, the curable composition further comprises photoinitiators, in an amount between the range of about 0.1% and about 5% by weight.

Useful photoinitiators include those known as useful for photocuring free-radically polyfunctional (meth)acrylates. Exemplary photoinitiators include benzoin and its derivatives such as alpha-methylbenzoin; alpha-phenylbenzoin; alpha-allylbenzoin; alpha-benzylbenzoin; benzoin ethers such as benzil dimethyl ketal (e.g., "IRGACURE 651" from BASF, Florham Park, N.J.), benzoin methyl ether, benzoin ethyl ether, benzoin n-butyl ether; acetophenone and its derivatives such as 2-hydroxy-2-methyl-1-phenyl-1-propanone (e.g., "DAROCUR 1173" from BASF, Florham Park, N.J.) and 1-hydroxycyclohexyl phenyl ketone (e.g., "IRGACURE 184" from BASF, Florham Park, N.J.); 2-methyl-1-[4-(methylthio)phenyl]-2-(4-morpholinyl)-1-propanone (e.g., "IRGACURE 907" from BASF, Florham Park, N.J.); 2-benzyl-2-(dimethylamino)-1-[4-(4-morpholinyl)phenyl]-1-butanone (e.g., "IRGACURE 369" from BASF, Florham Park, N.J.) and phosphine oxide derivatives such as Ethyl-2,4,6-trimethylbenzoylphenylphoshinate (e.g. "TPO-L" from BASF, Florham Park, N.J.), and Irgacure 819 (phenylbis(2,4,6-trimethylbenzoyl)phosphine oxide) available from BASF, Florham Park, N.J.

Other useful photoinitiators include, for example, pivaloin ethyl ether, anisoin ethyl ether, anthraquinones (e.g., anthraquinone, 2-ethylanthraquinone, 1-chloroanthraquinone, 1,4-dimethylanthraquinone, 1-methoxyanthraquinone, or benzanthraquinone), halomethyltriazines, benzophenone and its derivatives, iodonium salts and sulfonium salts, titanium complexes such as bis(etas-2,4-cyclopentadien-1-yl)-bis[2,6-difluoro-3-(1H-pyrrol-1-yl) phenyl]titanium (e.g., "CGI 784DC" from BASF, Florham Park, N.J.); halomethyl-nitrobenzenes (e.g., 4-bromomethylnitrobenzene), mono- and bis-acylphosphines (e.g., "IRGACURE 1700", "IRGACURE 1800", "IRGACURE 1850", and "DAROCUR 4265").

The curable composition may be irradiated with activating UV or visible radiation to polymerize the components preferably in the wavelengths of 250 to 500 nanometers. UV light sources can be of two types: 1) relatively low light intensity sources such as blacklights that provide generally 10 mW/cm$^2$ or less (as measured in accordance with procedures approved by the United States National Institute of Standards and Technology as, for example, with a UVIMAP™ UM 365 L-S radiometer manufactured by Electronic Instrumentation & Technology, Inc., in Sterling, Va.) over a wavelength range of 280 to 400 nanometers and 2) relatively high light intensity sources such as medium- and high-pressure mercury arc lamps, electrodeless mercury lamps, light emitting diodes, mercury-xenon lamps, lasers and the like, which provide intensities generally between 10 and 5000 mW/cm$^2$ in the wavelength rages of 320-390 nm (as measured in accordance with procedures approved by the United States National Institute of Standards and Technology as, for example, with a PowerPuck™ radiometer manufactured by Electronic Instrumentation & Technology, Inc., in Sterling, Va.).

Referring to FIG. 1, quantum dot article 10 includes a first barrier layer 32, a second barrier layer 34, and a quantum dot layer 20 between the first barrier layer 32 and the second barrier layer 34. The quantum dot layer 20 includes a plurality of quantum dots 22 dispersed in a matrix 24.

The barrier layers 32, 34 can be formed of any useful material that can protect the quantum dots 22 from exposure to environmental contaminates such as, for example, oxygen, water, and water vapor. Suitable barrier layers 32, 34 include, but are not limited to, films of polymers, glass and dielectric materials. In some embodiments, suitable materials for the barrier layers 32, 34 include, for example, polymers such as polyethylene terephthalate (PET); oxides such as silicon oxide, titanium oxide, or aluminum oxide (e.g., $SiO_2$, $Si_2O_3$, $TiO_2$, or $Al_2O_3$); and suitable combinations thereof.

More particularly, barrier films can be selected from a variety of constructions. Barrier films are typically selected such that they have oxygen and water transmission rates at a specified level as required by the application. In some embodiments, the barrier film has a water vapor transmission rate (WVTR) less than about 0.005 g/m$^2$/day at 38° C. and 100% relative humidity; in some embodiments, less than about 0.0005 g/m$^2$/day at 38° C. and 100% relative humidity; and in some embodiments, less than about 0.00005 g/m$^2$/day at 38° C. and 100% relative humidity. In some embodiments, the flexible barrier film has a WVTR of less than about 0.05, 0.005, 0.0005, or 0.00005 g/m$^2$/day at 50° C. and 100% relative humidity or even less than about 0.005, 0.0005, 0.00005 g/m$^2$/day at 85° C. and 100% relative humidity. In some embodiments, the barrier film has an oxygen transmission rate of less than about 0.005 g/m$^2$/day at 23° C. and 90% relative humidity; in some embodiments, less than about 0.0005 g/m$^2$/day at 23° C. and 90% relative humidity; and in some embodiments, less than about 0.00005 g/m$^2$/day at 23° C. and 90% relative humidity.

Exemplary useful barrier films include inorganic films prepared by atomic layer deposition, thermal evaporation, sputtering, and chemical vapor deposition. Useful barrier films are typically flexible and transparent. In some embodiments, useful barrier films comprise inorganic/organic. Flexible ultra-barrier films comprising inorganic/organic multilayers are described, for example, in U.S. Pat. No. 7,018,713 (Padiyath et al.). Such flexible ultra-barrier films may have a first polymer layer disposed on polymeric film substrate that is overcoated with two or more inorganic barrier layers separated by at least one second polymer layer. In some embodiments, the barrier film comprises one inorganic barrier layer interposed between the first polymer layer disposed on the polymeric film substrate and a second polymer layer 224.

In some embodiments, each barrier layer 32, 34 of the quantum dot article 10 includes at least two sub-layers of different materials or compositions. In some embodiments, such a multi-layered barrier construction can more effectively reduce or eliminate pinhole defect alignment in the barrier layers 32, 34, providing a more effective shield against oxygen and moisture penetration into the matrix 24. The quantum dot article 10 can include any suitable material or combination of barrier materials and any suitable number of barrier layers or sub-layers on either or both sides of the quantum dot layer 20. The materials, thickness, and number of barrier layers and sub-layers will depend on the particular application, and will suitably be chosen to maximize barrier protection and brightness of the quantum dots 22 while minimizing the thickness of the quantum dot article 10. In some embodiments each barrier layer 32, 34 is itself a laminate film, such as a dual laminate film, where each barrier film layer is sufficiently thick to eliminate wrinkling in roll-to-roll or laminate manufacturing processes. In one illustrative embodiment, the barrier layers 32, 34 are polyester films (e.g., PET) having an oxide layer on an exposed surface thereof.

The quantum dot layer 20 can include one or more populations of quantum dots or quantum dot materials 22. Exemplary quantum dots or quantum dot materials 22 emit green light and red light upon down-conversion of blue primary light from a blue LED to secondary light emitted by the quantum dots. The respective portions of red, green, and blue light can be controlled to achieve a desired white point for the white light emitted by a display device incorporating the quantum dot article 10. Exemplary quantum dots 22 for use in the quantum dot articles 10 include, but are not limited to, InP or CdSe with ZnS shells. Suitable quantum dots for use in quantum dot articles described herein include, but are not limited to, core/shell luminescent nanocrystals including CdSe/ZnS, InP/ZnS, PbSe/PbS, CdSe/CdS, CdTe/CdS or CdTe/ZnS. In exemplary embodiments, the luminescent nanocrystals include an outer ligand coating and are dispersed in a polymeric matrix. Quantum dot and quantum dot materials 22 are commercially available from, for example, Nanosys Inc., Milpitas, Calif. The quantum dot layer 20 can have any useful amount of quantum dots 22, and in some embodiments the quantum dot layer 20 can include from 0.1 wt % to 1 wt % quantum dots, based on the total weight of the quantum dot layer 20.

In one or more embodiments the quantum dot layer 20 can optionally include scattering beads or particles. These scattering beads or particles have a refractive index that differs from the refractive index of the matrix material 24 by at least 0.05, or by at least 0.1. These scattering beads or particles can include, for example, polymers such as silicone, acrylic, nylon, and the like, or inorganic materials such as $TiO_2$, $SiO_x$, $AlO_x$, and the like, and combinations thereof. In some embodiments, including scattering particles in the quantum dot layer 20 can increase the optical path length through the quantum dot layer 20 and improve quantum dot absorption and efficiency. In many embodiments, the scattering beads or particles have an average particle size from 1 to 10 micrometers, or from 2 to 6 micrometers. In some embodiments, the quantum dot material 20 can optionally include fillers such fumed silica.

In some preferred embodiments, the scattering beads or particles are Tospearl™ 120A, 130A, 145A and 2000B spherical silicone resins available in 2.0, 3.0, 4.5 and 6.0 micron particle sizes respectively from Momentive Specialty Chemicals Inc., Columbus, Ohio.

The matrix 24 of the quantum dot layer 20 can be formed from a polymeric binder or binder precursor that adheres to the materials forming the barrier layers 32, 34 to form a laminate construction, and also forms a protective matrix for the quantum dots 22. In one embodiment, the matrix 24 is formed by curing or hardening an adhesive composition including an epoxy amine polymer and an optional radiation-curable methacrylate compound.

Figure 2:
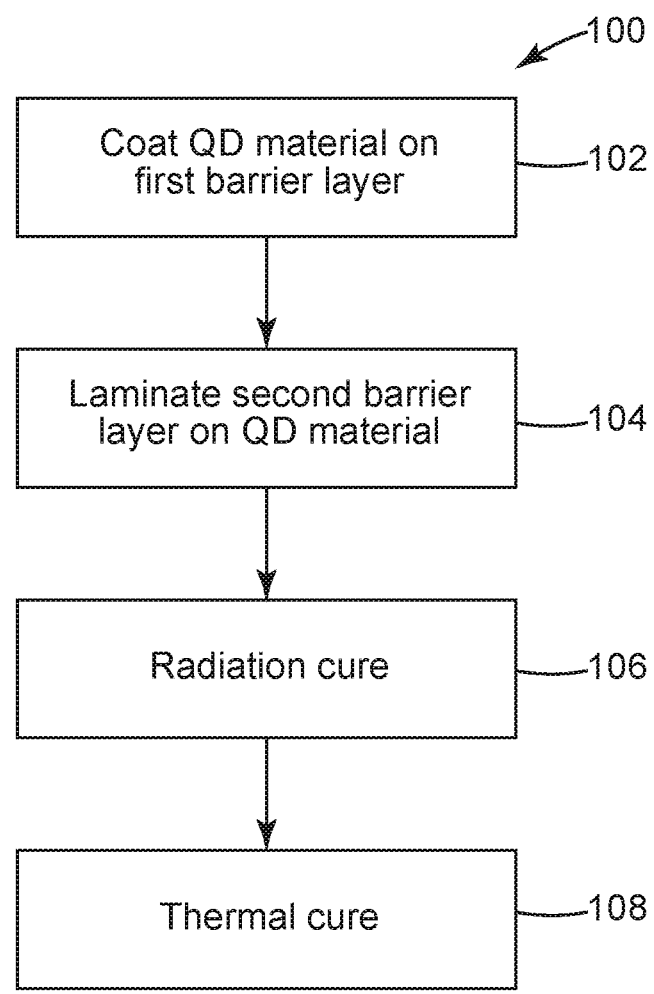
FIG. 2 is a flow diagram of an illustrative method of forming a quantum dot film.

Referring to FIG. 2, in another aspect, the present disclosure is directed to a method of forming a quantum dot film article 100 including coating an adhesive composition including quantum dots on a first barrier layer 102 and disposing a second barrier layer on the quantum dot material 104. In some embodiments, the method 100 includes polymerizing (e.g., radiation curing) the radiation curable polymeric binder to form a fully- or partially cured quantum dot material 106 and optionally thermally polymerizing the binder composition to form a cured polymeric binder 108. For thermally curable polymeric binders, step 106 is omitted.

In some embodiments, the binder composition can be cured or hardened by heating. In other embodiments, the adhesive composition may also be cured or hardened by applying radiation such as, for example, ultraviolet (UV) light. Curing or hardening steps may include UV curing, heating, or both. In some example embodiments that are not intended to be limiting, UV cure conditions can include applying about 10 mJ/cm² to about 4000 mJ/cm² of UVA, more preferably about 10mJ/cm² to about 200 mJ/cm² of UVA. Heating and UV light may also be applied alone or in combination to increase the viscosity of the binder composition, which can allow easier handling on coating and processing lines.

In some embodiments, the binder composition may be cured after lamination between the overlying barrier films 32, 34. Thus, the increase in viscosity of the binder composition locks in the coating quality right after lamination. By curing right after coating or laminating, in some embodiments the cured binder increases in viscosity to a point that the binder composition acts as a pressure sensitive adhesive (PSA) to hold the laminate together during the cure and greatly reduces defects during the cure. In some embodiments, the radiation cure of the binder provides greater control over coating, curing and web handling as compared to traditional thermal curing.

Once at least partially cured, the binder composition forms polymer network that provides a protective supporting matrix 24 for the quantum dots 22.

Ingress, including edge ingress, is defined by a loss in quantum dot performance due to ingress of moisture and/or oxygen into the matrix 24. In various embodiments, the edge ingress of moisture and oxygen into the cured matrix 24 is less than about 1.25 mm after 1 week at 85° C., or about less than 0.75 mm after 1 week at 85° C., or less than about 0.5 mm after 1 week at 85° C. In various embodiments, oxygen permeation into the cured matrix is less than about 80 (cc·mil)/(m² day), or less than about 50 (cc·mil)/(m² day). In various embodiments, the water vapor transmission rate of the cured matrix should be less than about 15 (20 g/m²·mil·day), or less than about 10 (20 g/m²·mil·day).

In various embodiments, the thickness of the quantum dot layer 20 is about 80 microns to about 250 microns.

Figure 3:
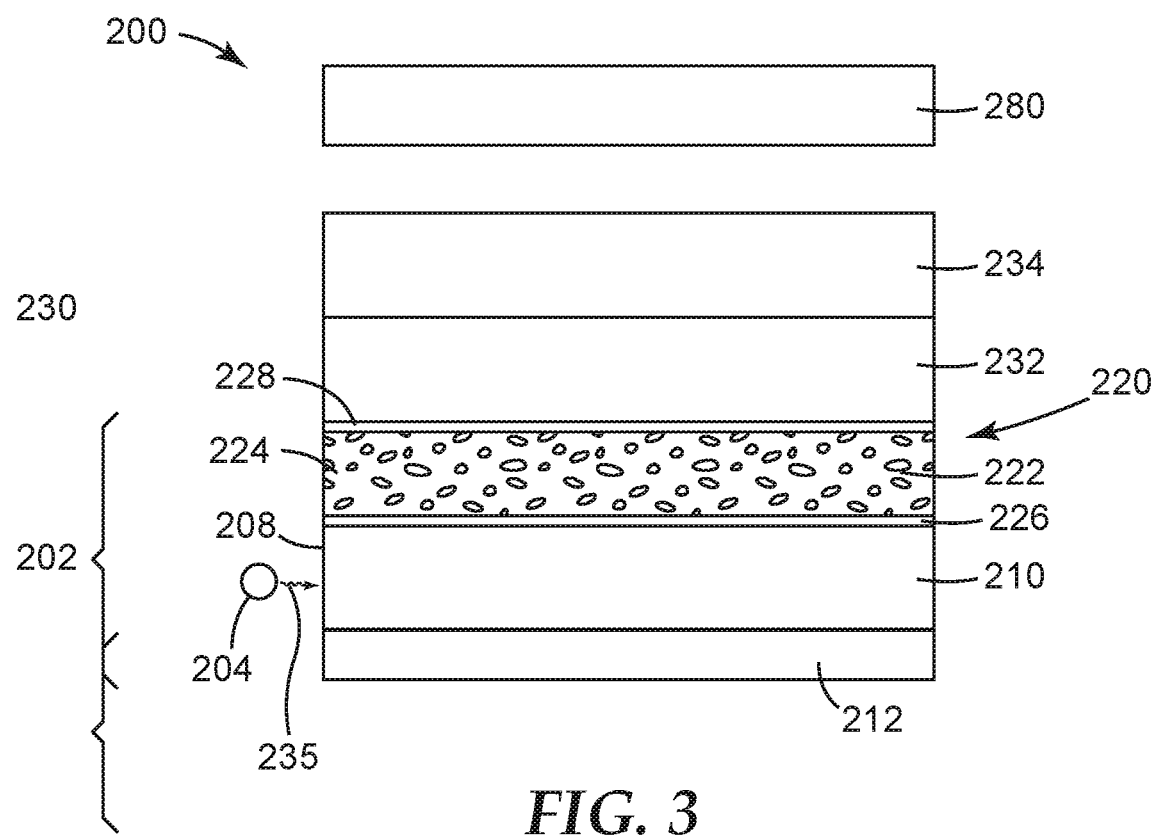
FIG. 3 is a schematic illustration of an embodiment of a display including a quantum dot article.

FIG. 3 is a schematic illustration of an embodiment of a display device 200 including the quantum dot articles described herein. This illustration is merely provided as an example and is not intended to be limiting. The display device 200 includes a backlight 202 with a light source 204 such as, for example, a light emitting diode (LED). The light source 204 emits light along an emission axis 235. The light source 204 (for example, a LED light source) emits light through an input edge 208 into a hollow light recycling cavity 210 having a back reflector 212 thereon. The back reflector 212 can be predominately specular, diffuse or a combination thereof, and is preferably highly reflective. The backlight 202 further includes a quantum dot article 220, which includes a protective matrix 224 having dispersed therein quantum dots 222. The protective matrix 224 is bounded on both surfaces by polymeric barrier films 226, 228, which may include a single layer or multiple layers.

The display device 200 further includes a front reflector 230 that includes multiple directional recycling films or layers, which are optical films with a surface structure that redirects off-axis light in a direction closer to the axis of the display, which can increase the amount of light propagating on-axis through the display device, this increasing the brightness and contrast of the image seen by a viewer. The front reflector 230 can also include other types of optical films such as polarizers. In one non-limiting example, the front reflector 230 can include one or more prismatic films 232 and/or gain diffusers. The prismatic films 232 may have prisms elongated along an axis, which may be oriented parallel or perpendicular to an emission axis 235 of the light source 204. In some embodiments, the prism axes of the prismatic films may be crossed. The front reflector 230 may further include one or more polarizing films 234, which may include multilayer optical polarizing films, diffusely reflecting polarizing films, and the like. The light emitted by the front reflector 230 enters a liquid crystal (LC) panel 280. Numerous examples of backlighting structures and films may be found in, for example, U.S. Pat. No. 8,848,132 (O'Neill et al.).

EXAMPLES

TABLE 1

Materials

| Material | Description |
| --- | --- |
| Quantum Dots | InP core/ZnS shell quantum dots were obtained from Nanosys, Inc (Milpitas, CA). "Green growth solution" describes a dispersion of green-emitting InP quantum dots with a zinc sulfide shell dispersed in octadecene with an optical density (optical density, OD, is defined as the absorbance at 440 nm with a 1 cm cell path length) of 10. "Red growth solution" describes a similar dispersion of red-emitting quantum dots, also with an OD of 10. The quantum dot dispersions were stored and handled in an inert atmosphere glove box. |
| FC-70 | A high-boiling perfluorinated fluid available from 3M (St. Paul, MN) under trade designation "FLUORINERT ELECTRONIC LIQUID FC-70." This material was deoxygenated with bubbling $N_2$ gas and stored in an inert atmosphere glove box. |
| PF-5052 | a fully fluorinated solvent available from 3M (St. Paul, MN) under trade designation "PERFORMANCE FLUID PF-5052". |
| Novec 7100 | a hydrofluoroether solvent available from 3M (St. Paul, MN) under trade designation "NOVEC 7100 ENGINEERED FLUID." |
| Novec 7200 | a hydrofluoroether solvent available from 3M (St. Paul, MN) under trade designation "NOVEC 7200 ENGINEERED FLUID." |
| Heptane | anhydrous grade obtained from Sigma Aldrich (St. Louis, MO) and was stored in an inert atmosphere glove box. |
| Vazo-67 | A solid thermal radical initiator available from Dupont (Wilmington, DE). |

Reagents and solvents not listed in table 1 were obtained from standard chemical suppliers such as Sigma Aldrich (St Louis, Mo.) and were used as received.

Preparative Example 1: Preparation of HFPO-Derived Methyl Ester

The methyl ester $F(CF(CF_3)CF_2O)_aCF(CF_3)C(O)OCH_3$, wherein the variable a has an average value of about 6, was prepared by metal fluoride-initiated oligomerization of hexafluoropropylene oxide (HFPO) in diglyme solvent according to the method described in U.S. Pat. No. 3,250,808 (Moore et al.), the description of which is incorporated herein by reference. The product was purified by distillation to remove low-boiling components.

Preparative Example 2: Preparation of HFPO-Derived Alcohol

The alcohol $F(CF(CF_3)CF_2O)_aCF(CF_3)CH_2OH$, wherein the variable a has an average value of about 6, was prepared by sodium borohydride reduction of the methyl ester of Preparative Example 1 according to the method described in US Patent Publication No. 2014-0287248 (Flynn et. al.), the description of which is incorporated herein by reference.

Preparative Example 3: Preparation of HFPO-Derived Allyl Ether

The allyl ether $F(CF(CF_3)CF_2O)_aCF(CF_3)CH_2OCH_2CHCH_2$, wherein the variable a has an average value of about 6, was prepared from the alcohol of Preparative Example 2 by reaction with allyl bromide according to the method described in US Patent Publication No. 2014-0287248 (Flynn et. al.), the description of which is incorporated herein by reference.

Example 1: Preparation of HFPO-Derived Ether Succinic Acid

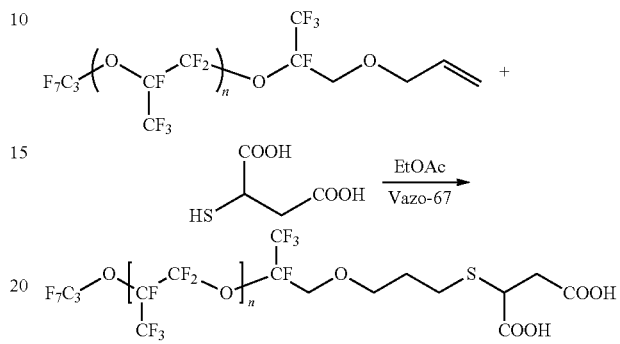

A flask with condenser attached was charged with the polymer of Preparative Example 3 (5.0 g, 3.5 mmol), ethyl acetate (20 mL), mercaptosuccinic acid (0.79 g, 5.3 mmol), and Vazo-67 (100 mg, 0.53 mmol). The mixture was deoxygenated by bubbling $N_2$ through the liquid for 15 min. The solution was then heated to reflux and stirred overnight. The solvent was removed by rotary evaporation at reduced pressure, and the product was dissolved in 50 mL of PF-5052. The solution was washed three times with 70 mL of a 5:2 isopropanol:water mixture (by volume). The solvent was removed by rotary evaporation at reduced pressure to yield 4.5 g of clear viscous oil.

Example 2: Preparation of an HFPO-Derived Ester Phosphine

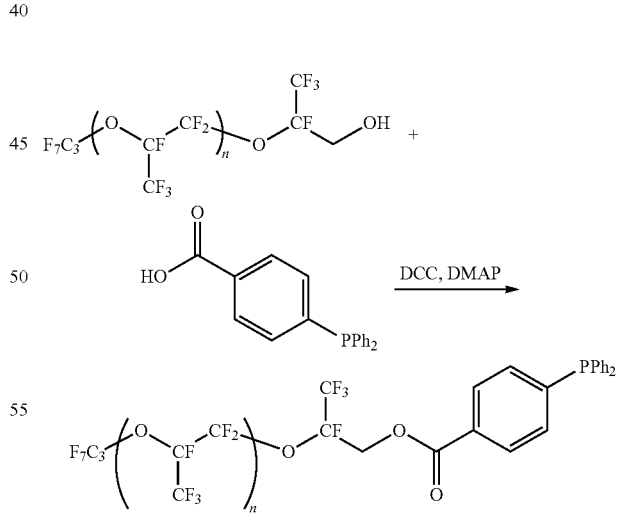

A flask with condenser attached was charged with poly (HFPO) alcohol of Preparative Example 2 (5.0 g, 3.8 mmol), 4-(diphenylphosphino)benzoic acid (1.41 g, 4.6 mmol), 4-dimethylaminopyridine (47 mg, 0.38 mmol), activated 3 Å molecular sieves (1 g), Novec 7200 (15 mL), and dichloromethane (10 mL). This mixture was stirred for 30 minutes at room temperature. A 1.0M solution of dicyclohexylcarbodiimide in dichloromethane (4.6 mL, 4.6 mmol) was added by syringe. The solution was then heated to reflux and stirred overnight, resulting in the formation of a white precipitate. After cooling to room temperature, the mixture was diluted with PF-5052 (100 mL), isopropanol (80 mL), and water (20 mL). The liquids were decanted to remove solid sieves, and the layers were separated. The fluorinated layer was then washed twice with a 4:1 mixture of isopropanol:water (2×100 mL) and then concentrated by rotary evaporation at reduced pressure to yield a light yellow oil (6.0 g, 98% yield).

Example 3: Preparation of HFPO-Derived Ether Thioester

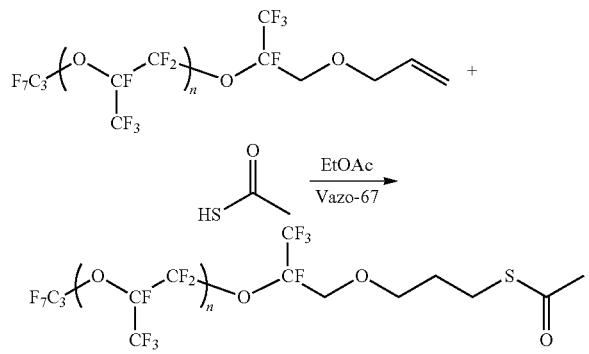

A flask with condenser attached was charged with the polymer of Preparative Example 3 (20.0 g, 14.0 mmol), ethyl acetate (50 mL), Novec 7100 (30 mL), thioacetic acid (1.60 g, 21.0 mmol), and Vazo-67 (400 mg, 2.1 mmol). The mixture was deoxygenated by bubbling $N_2$ through the liquid for 15 min. The solution was then heated to reflux and stirred overnight. The solvent was removed by rotary evaporation at reduced pressure, and the product was dissolved in 100 mL of PF-5052. The solution was washed three times with 140 mL of a 5:2 isopropanol:water mixture (by volume). The solvent was removed by rotary evaporation at reduced pressure to yield 19 g of clear oil.

Example 4: Preparation of HFPO-Derived Ether Thiol

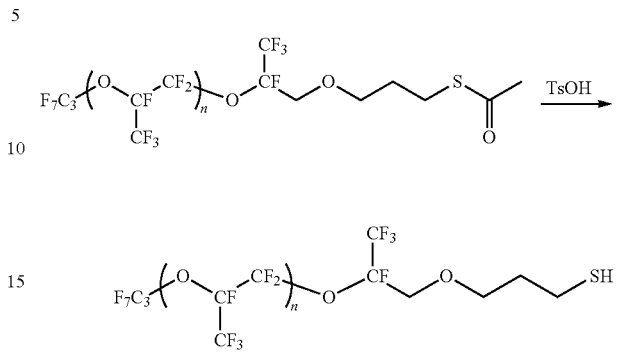

A flask with condenser attached was charged with the polymer of Example 3 (15.0 g, 10.5 mmol), Novec 7100 (20 mL), methanol (10 mL), and p-toluenesulfonic acid (2.0 g, 10.5 mmol). The solution was heated to reflux overnight. The solvent was removed by rotary evaporation at reduced pressure, and the product was dissolved in 50 mL of PF-5052. The solution was washed three times with 50 mL of isopropanol. The solvent was removed by rotary evaporation at reduced pressure to yield 14 g of clear oil.

Example 5: Preparation of HFPO-Derived Ether Thioether Phosphine

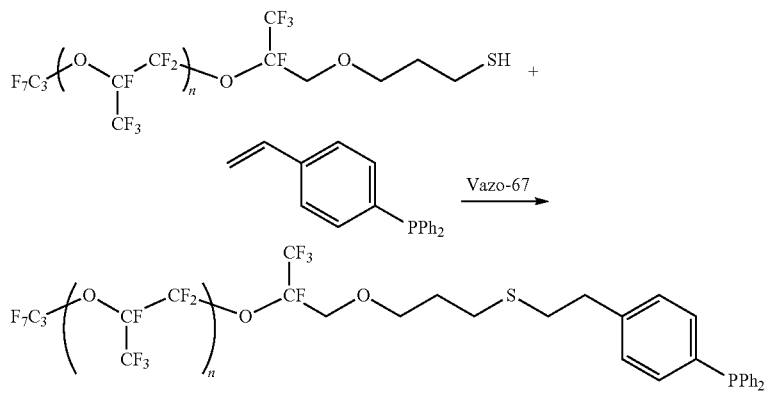

A flask with condenser attached was charged with the polymer of Example 4 (2.0 g, 1.5 mmol), 4-(diphenylphosphino)styrene (421 mg, 1.5 mmol), and ethyl acetate (10 mL). The biphasic mixture was degassed with bubbling $N_2$ for 10 minutes, then heated in an oil bath held at 70° C. until a single homogenous phase was observed. Solid Vazo-67 (28 mg, 0.15 mmol) was then added at once. The solution was heated in the oil bath overnight. The ethyl acetate was removed by rotary evaporation at reduced pressure, and the product was dissolved in 10 mL of PF-5052. The solution was washed three times with 10 mL of a 4:1 isopropanol:water mixture (by volume). The solvent was removed by rotary evaporation at reduced pressure to yield a light yellow oil.

Example 6: Preparation of a Green and Red InP/ZnS Dispersion in FC-70

A 1:1 mixture by mass of the polymer of Example 1 and FC-70 was degassed using bubbling nitrogen and then placed in an inert atmosphere glovebox. A 100 mL round bottomed flask was charged with the above solution (5 mL), FC-70 (5 mL), green growth solution (30 mL), and red growth solution (15 mL). The flask was placed in an aluminum heating block on a hot plate held at 80° C. The mixture was stirred vigorously for 2 hours, after which it was allowed to cool and separate into 2 layers overnight. The colorless top layer was removed, and the bottom fluorinated layer was washed twice with 30 mL of heptane, stirring for 5 minutes during each washing. Residual heptane was removed under low pressure, yielding a haze-free orange-red oil with an OD of approximately 45.

Example 7: Stability to Light Exposure of InP Concentrate Dispersions

Figure 4:
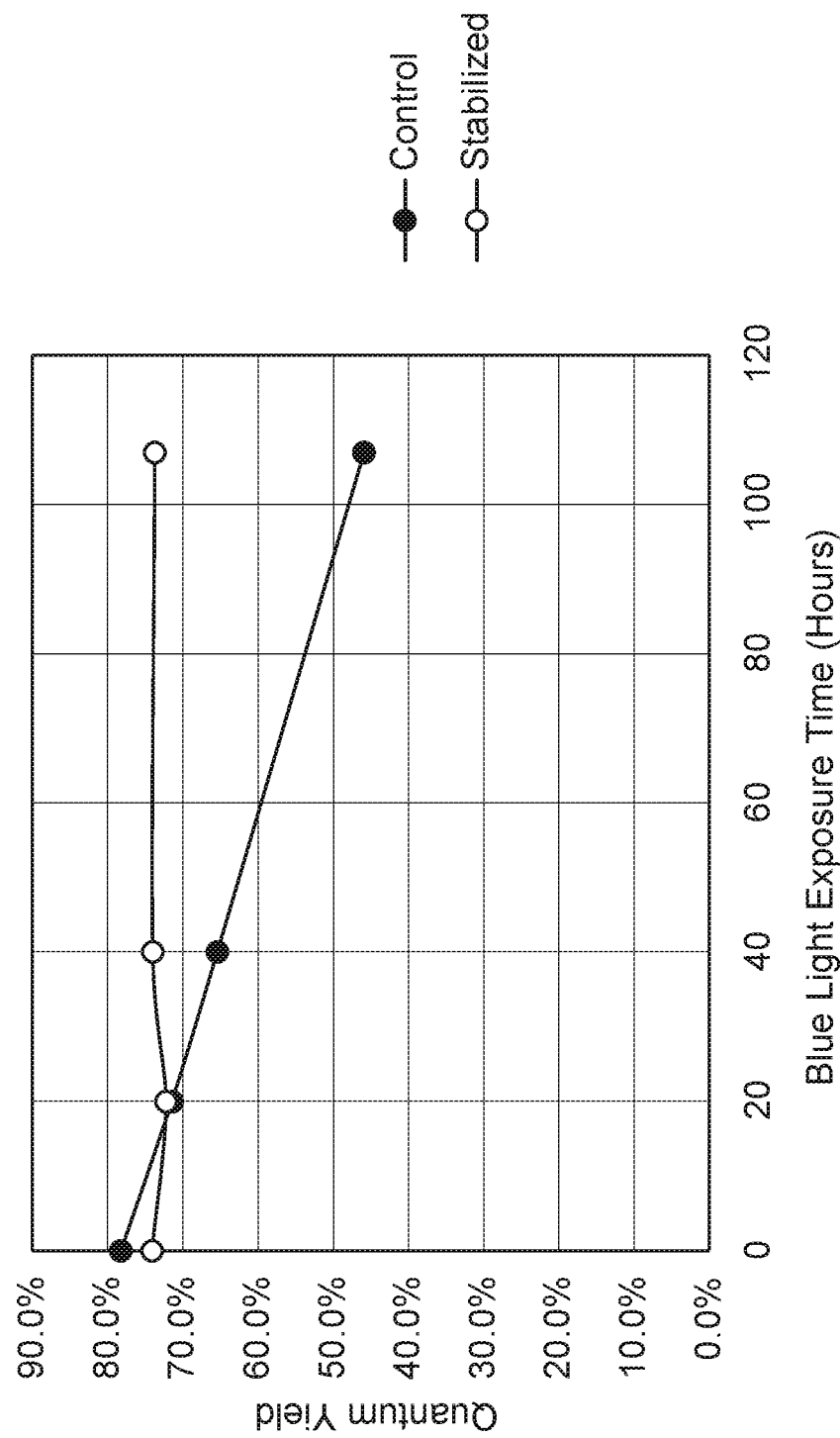
FIG. 4 is the quantum yield data of Example 7.

A 25% by mass solution of the polymer of Example 2 in FC-70 was degassed using bubbling nitrogen and then placed in an inert atmosphere glovebox. This solution was mixed in a 1:1 volume ratio with the quantum dot dispersion of Example 6 to create the "stabilized" quantum dot dispersion. A "control" dispersion was created by mixing the dispersion of Example 6 with FC-70 at a 1:1 volume ratio. The stabilized and control dispersions were separately placed in septum-capped quartz cuvettes with a cell of width 1 cm and length 0.1 cm. These cells were placed in a lamp between two 15 watt Phillips TLD fluorescent bulbs with a spectral output in the blue range. The lamp was covered with reflective foil and turned on. At specified times, 12 μL aliquots of concentrate were removed from the cuvettes and diluted with 4 mL of FC-70. Quantum yields of these dilute dispersions were measured using an absolute PL Quantum Yield Spectrometer C11347 (Hamamatsu Corporation, Middlesex, N.J.). The results are shown in FIG. 4.

What is claimed is:

1. A composite particle comprising a fluorescent semiconductor core/shell nanoparticle and
a stabilizing agent of the formula:

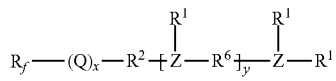

wherein each $R^1$ is a hydrocarbyl group including alkyl, aryl, alkaryl and aralkyl;
$R^2$ is a divalent hydrocarbyl group selected from alkylene, arylene, alkarylene and aralkylene;
Z is P, As or Sb;
Q is $-CH_2-S-$, $-CH_2-O-$, $-CO_2-$, $-CH2-O-CO-$, $-CONR^3-$, $-NH-CO-NR^3-$, and $-NR^3$, where $R^3$ is H or $C_1$-$C_4$ alkyl,
subscript x is 1,
$R^6$ is a divalent hydrocarbyl group selected from alkylene, arylene, alkarylene and aralkylene,
subscript y is 0 or 1,
$R_f$ is a perfluoroether group.

2. The composite particle of claim 1 wherein $R_f$ is of the formula $C_aF_{2a+1}-(O-C_bF_{2b})_c-$, where a is at least 1, b is at least 1 and c may be a number from 1 to 50.

3. The composite particle of claim 2 wherein each of subscripts a and b are 1 to 6.

4. The composite particle of claim 1 wherein $R_f$ is a perfluoropolyether having perfluorinated repeating units selected from the group of $-(C_pF_{2p})-$, $-(C_pF_{2p}O)-$, $-(CF(R_f^2))-$, $-(CF(R_f^2)O)-$, $-(CF(R_f^2)C_pF_{2p}O)-$, $-(C_pF_{2p}CF(R_f^2)O)-$, $-(CF_2CF(R_f^2)O)-$, where p is an integer of 1 to 10 and $R_f^2$ is a fluorine atom, perfluoroalkyl group, perfluoroether group, nitrogen-containing perfluoroalkyl group, perfluoropolyether, or a perfluoroalkoxy group.

5. The composite particle of claim 1 wherein at least one of said $R^1$ groups is an aryl or alkaryl group.

6. The composite particle of claim 1 wherein two of said $R^1$ groups are an aryl or alkaryl group.

7. The composite particle of claim 1 wherein $R^1$ is phenyl.

8. The composite particle of claim 1 wherein $R^2$ is phenylene.

9. The composite particle of claim 1 further comprising a surface modifying ligand bound to the surface of the nanoparticle of the formula:

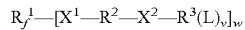

wherein
$R_f^1$ is a fluorochemical group of valence w selected from perfluoroalkane, perfluoroether or perfluoropolyether,
$R^2$ is a hydrocarbyl group including alkylene, arylene, alkarylene and aralkylene;
$R^3$ is a hydrocarbyl group including alkylene, arylene, alkarylene and aralkylene;
$X^1$ is $-CH_2-O-$, $-O-$, $-CO_2-$, $-CONR^1-$, or $-SO_2NR^{1-}$ where $R^1$ is H or $C_1$-$C_4$ alkyl;
$X^2$ is a covalent bond, $-S-$, $-O-$, $-NR^1-$, $-CO_2-$, $-CONR^1-$, or $-SO_2NR^{1-}$ where $R^1$ is H or $C_1$-$C_4$ alkyl;
v at least one;
w is 1 or 2
L is an ligand group selected from $-CO_2H$, $-SH$, $-P(O)(OH)_2$, $-P(O)OH$, $-NH_2$, $-OH$, and $-SO_3H$.

10. The composite particle of claim 1 wherein the core comprises InP, CdS or CdSe.

11. The composite particle of claim 1 wherein the shell comprises a magnesium or zinc-containing compound.

12. The composite particle of claim 1 wherein the shell is a multilayered shell.

13. The composite particle of claim 12 wherein the multilayered shell comprises an inner shell overcoating the core, wherein the inner shell comprises zinc selenide and zinc sulfide.

14. The composite particle of claim 12 wherein the multilayered shell comprises an outer shell overcoating an inner shell, wherein the outer shell comprises zinc sulfide or MgS.

15. A composite particle comprising:
a fluorescent semiconductor core/shell nanoparticle comprising:
an InP core;
an inner shell overcoating the core, wherein the inner shell comprises zinc selenide and zinc sulfide; and
an outer shell overcoating the inner shell, wherein the outer shell comprises zinc sulfide; and a stabilizing agent of the formula:

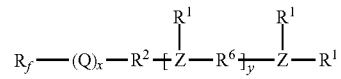

wherein each $R^1$ is a hydrocarbyl group including alkyl, aryl, alkaryl and aralkyl;

$R^2$ is a divalent hydrocarbyl group selected from alkylene, arylene, alkarylene and aralkylene;

Z is P, As or Sb;

Q is $-CH_2-S-$, $-CH_2-O-$, $-CO_2-$, $-CH2-O-CO-$, $-CONR^3-$, $-NH-CO-NR^3-$, and $-NR^3$, where $R^3$ is H or $C_1$-$C_4$ alkyl, subscript x is 1, $R^6$ is a divalent hydrocarbyl group selected from alkylene, arylene, alkarylene and aralkylene, subscript y is 0 or 1, and $R_f$ is a perfluoroether group.

16. A composition comprising the composite particle of claim 1 further comprising a secondary fluorochemical carrier fluid.

17. A composition comprising the composite particle of claim 1 dispersed in droplets of a secondary fluorochemical carrier fluid, said droplets dispersed in a polymeric binder.

18. The composition of claim 17 wherein the polymeric binder comprises polysiloxanes, fluoroelastomers, polyamides, polyimides, polycaprolactones, polycaprolactams, polyurethanes, polyvinyl alcohols, polyvinyl chlorides, polyvinyl acetates, polyesters, polycarbonates, polyacrylates, polymethacrylates, polyacrylamides, epoxy resins and polymethacrylamides.

19. An article comprising the composite particle of claim 1 dispersed in the cured polymeric binder between two barrier films.

20. The article of claim 19 wherein the polymeric binder comprises polysiloxanes, fluoroelastomers, polyamides, polyimides, polycaprolactones, polycaprolactams, polyurethanes, polyvinyl alcohols, polyvinyl chlorides, polyvinyl acetates, polyesters, polycarbonates, polyacrylates, polymethacrylates, polyacrylamides, epoxy resins and polymethacrylamides.

21. A quantum dot film article comprising:
a first barrier layer;
a second barrier layer; and
a quantum dot layer between the first barrier layer and the second barrier layer, the quantum dot layer comprising the composite particles of claim 1, the composite particles dispersed in a polymeric binder.

22. The quantum dot film article of claim 21 wherein the quantum dot layer comprises dispersed droplets of composite particles in fluoropolymer carrier fluid.

23. A composition comprising
a. 1 to 10 parts by weight of fluorescent semiconductor core/shell nanoparticles,
b. 1 to 40 parts by weight of a stabilizing agent of the formula:

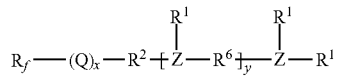

wherein each $R^1$ is a hydrocarbyl group including alkyl, aryl, alkaryl and aralkyl;

$R^2$ is a divalent hydrocarbyl group selected from alkylene, arylene, alkarylene and aralkylene;

Z is P, As or Sb;

Q is $-CH_2-S-$, $-CH_2-O-$, $-CO_2-$, $-CH_2-O-CO-$, $-CONR^3-$, $-NH-CO-NR^3-$, and $-NR^3$, where $R^3$ is H or $C_1$-$C_4$ alkyl, and subscript x is 1, $R^6$ is a divalent hydrocarbyl group selected from alkylene, arylene, alkarylene and aralkylene, subscript y is 0 or 1, $R_f$ is a perfluoroether group, and c. 5 to 50 parts by weight of a secondary perfluorinated carrier fluid.

24. The composition of claim 23 dispersed in a polymeric binder.

* * * * *